United States Patent [19]

Luly et al.

[11] Patent Number: 5,214,129
[45] Date of Patent: May 25, 1993

[54] PEPTIDYLAMINODIOLS

[75] Inventors: Jay R. Luly; Jacob J. Plattner, both of Libertyville; Dale J. Kempf, Lake Villa, all of Ill.

[73] Assignee: Abbott Laboratories, Abbott Park, Ill.

[21] Appl. No.: 793,773

[22] Filed: Nov. 18, 1991

Related U.S. Application Data

[60] Division of Ser. No. 713,644, Jun. 10, 1991, Pat. No. 5,091,575, which is a continuation of Ser. No. 327,467, Mar. 22, 1989, abandoned, which is a division of Ser. No. 217,106, Jul. 11, 1988, Pat. No. 4,845,079, which is a continuation of Ser. No. 943,567, Dec. 31, 1986, abandoned, which is a continuation-in-part of Ser. No. 895,009, Aug. 7, 1986, abandoned, which is a continuation-in-part of Ser. No. 818,734, Jan. 16, 1986, abandoned, which is a continuation-in-part of Ser. No. 693,951, Jan. 23, 1985, abandoned.

[51] Int. Cl.$^5$ .................. C07C 211/03; C07C 271/12
[52] U.S. Cl. .................. 530/331; 560/115; 564/336; 564/507
[58] Field of Search ............... 564/336, 507; 560/115; 530/331

[56] References Cited

U.S. PATENT DOCUMENTS

| 4,548,926 | 10/1985 | Matsueda et al. | 514/18 |
| 4,657,931 | 4/1987 | Baran et al. | 530/331 |
| 5,091,575 | 2/1992 | Luly et al. | 560/115 |

FOREIGN PATENT DOCUMENTS

| 189203 | 7/1986 | European Pat. Off. |
| 211580 | 2/1987 | European Pat. Off. |
| 266950 | 5/1988 | European Pat. Off. |
| WO88/05050 | 7/1988 | European Pat. Off. |

OTHER PUBLICATIONS

Chemical Abstracts 79:105010. Pansevich-Kolyada et al., Oxide Compounds Vesdi Akad. Navok Belaros. SSR, Ser, Khim., Navuk, 1973.
Chemical Astracts 87:38779. Stel'tsov et al., Studies on Epoxy Compounds, Vesti Akad Navuk Belarus, SSR, Ser. Khim. Navuk, 1977.

*Primary Examiner*—Ronald W. Griffin
*Attorney, Agent, or Firm*—Steven R. Crowley

[57] ABSTRACT

A renin inhibiting compound of the formula:

$$A\underset{R_1}{\overset{}{\diagdown}}\overset{R_3}{\underset{}{\diagdown}}W\underset{}{\overset{}{-}}U\underset{}{\overset{}{-}}\underset{O}{\overset{}{\diagdown}}\overset{H}{\underset{}{-}}N\underset{R_4}{\overset{R_8}{\diagdown}}\underset{R_9}{\overset{R_5}{\diagdown}}\overset{R_6}{\underset{R_7}{\diagdown}}$$

wherein A is a substituent; W is C=O or CHOH; U is $CH_2$ or $NR_2$, provided that when W is CHOH then U is $CH_2$; $R_1$ is loweralkyl, cycloalkylmethyl, benzyl, 4-methoxybenzyl, halobenzyl, (1-naphthyl)methyl, (2-naphthyl)methyl, (4-imidazoyl)methyl, α,α-dimethylbenzyl, 1-benzyloxyethyl, phenethyl, phenoxy, thiophenoxy or anilino; $R_2$ is hydrogen or loweralkyl; $R_3$ is loweralkyl, [(alkoxy)alkoxy]alkyl, (thioalkoxy)alkyl, loweralkenyl, benzyl or heterocyclic ring substituted methyl; $R_4$ is loweralkyl, cycloalkylmethyl or benzyl; $R_5$ is vinyl, formyl, hydroxymethyl or hydrogen; $R_7$ is hydrogen or loweralkyl; $R_8$ and $R_9$ are independently selected from OH and $NH_2$; and $R_6$ is hydrogen, loweralkyl, vinyl or arylalkyl; provided that when $R_5$ and $R_7$ are both hydrogen and $R_8$ and $R_9$ are OH, the carbon bearing $R_5$ is of the "R" configuration and the carbon bearing $R_6$ is of the "S" configuration; or pharmaceutically acceptable salts or esters thereof. Also disclosed are renin inhibiting compositions, a method of treating hypertension, methods of making the renin inhibiting compounds and intermediates useful in making the renin inhibiting compounds.

11 Claims, No Drawings

PEPTIDYLAMINODIOLS

This is a division of U.S. patent application Ser. No. 07/713,644, filed Jun. 10, 1991, U.S. Pat. No. 5,091,575, which is a continuation of U.S. patent application Ser. No. 07/327,467, filed Mar. 22, 1989, now abandoned, which is a division of U.S. patent application Ser. No. 07/217,106, filed Jul. 11, 1988, U.S. Pat. No. 4,845,079, which is a continuation of U.S. patent application Ser. No. 06/943,567, filed Dec. 31, 1986, now abandoned, which is a continuation-in-part of U.S. patent application Ser. No. 06/895,009, filed Aug. 7, 1986, now abandoned, which is a continuation-in-part of U.S. patent application Ser. No. 06/818,734, filed Jan. 16, 1986, now abandoned, which is a continuation-in-part of U.S. patent application Ser. No. 06/693,951, filed Jan. 23, 1985, now abandoned.

TECHNICAL FIELD

The present invention relates to novel organic compounds and compositions which inhibit renin, processes for making such compound, synthetic intermediates employed in these processes and a method of treating hypertension with such compounds.

BACKGROUND ART

Renin is a proteolytic enzyme synthesized and stored principally in a specific part of the kidney called the juxtaglomerular apparatus. Any of three different physiologic circumstances may cause the release of renin into the circulation: (a) a decrease in the blood pressure entering or within the kidney itself; (b) a decrease in the blood volume in the body; or (c) a fall in the concentration of sodium in the distal tubules of the kidney.

When renin is released into the blood from the kidney, the renin angiotensin system is activated, leading to vasoconstriction and conservation of sodium, both of which result in increased blood pressure. The renin acts on a circulating protein, angiotensinogen, to cleave out a fragment called angiotensin I (AI). AI itself has only slight pharmacologic activity, but, after additional cleavage by a second enzyme, angiotensin converting enzyme (ACE), forms the potent molecule angiotensin II (AII). The major pharmacological effects of AII are vasoconstriction and stimulation of the adrenal cortex to release aldosterone, a hormone which causes sodium retention. AII is cleaved by an aminopeptidase to form angiotensin III (AIII), which, compared to AII, is a less potent vasoconstrictor but a more potent inducer of aldosterone release.

Inhibitors of renin have been sought as agents for control of hypertension and as diagnostic agents for identification of cases of hypertension due to renin excess.

With these objectives in mind, the renin-angiotension system has been modulated or manipulated, in the past, with ACE inhibitors. However, ACE acts on several substrates other than angiotensin I (AI), most notably the kinins which cause such undesirable side effects as pain, "leaky" capillaries, prostaglandin release and a variety of behavioral and neurologic effects. Further, ACE inhibition leads to the accumulation of AI. Although AI has much less vasoconstrictor activity than AII, its presence may negate some of the hypotensive effects of the blockade of AII synthesis.

Inhibition of other targets in the renin-angiotensin system such as AII with compounds such as saralasin can block AII activity, but would leave unimpaired and perhaps enhance the hypertensive effects of AIII.

On the other hand, there are no known side effects which result when renin is inhibited from acting on its substrate. Considerable research efforts have thus been carried out to develop useful inhibitors of renin. Past research efforts have been directed to renin antibodies, pepstatin, phospholipids and substrate analogs such as tetrapeptides and octapeptides to tridecapeptides. These inhibitors either demonstrate poor activity in inhibiting renin production or poor specificity for inhibiting renin only. However, Boger et al. have reported that statine-containing peptides possess potent and specific renin-inhibiting activity (*Nature*, Vol. 303, p. 81, 1983). In addition, Szelke and co-workers have described polypeptide analogs containing a non-peptide link (*Nature*, Vol. 299, p. 555, 1982) which also cause potent renin inhibition and show a high specificity for this enzyme.

DISCLOSURE OF THE INVENTION

In accordance with the present invention, there are renin inhibiting compounds of the formula:

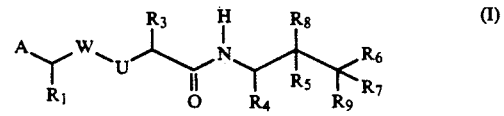

wherein A is hydrogen; loweralkyl; arylalkyl; $OR_{10}$ or $SR_{10}$ wherein $R_{10}$ is hydrogen, loweralkyl or aminoalkyl; $NR_{11}R_{12}$ wherein $R_{11}$ and $R_{12}$ are independently selected from hydrogen, loweralkyl, aminoalkyl, cyanoalkyl and hydroxyalkyl;

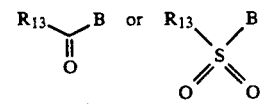

wherein B is NH, alkylamino, S, O, $CH_2$ or CHOH and $R_{13}$ is loweralkyl, cycloalkyl, aryl arylalkyl, alkoxy, alkenyloxy, hydroxyalkoxy, dihydroxyalkoxy, arylalkoxy, arylalkoxyalkyl, amino, alkylamino, dialkylamino, (hydroxyalkyl)(alkyl)amino, aminoalkyl, N-protected aminoalkyl, alkylaminoalkyl, (N-protected)(alkyl)aminoalkyl, dialkylaminoalkyl, (heterocyclic)alkyl or a substituted or unsubstituted heterocyclic;

W is C=O or CHOH;

U is $CH_2$ or $NR_2$, provided that when W is CHOH then U is $CH_2$;

$R_1$ is loweralkyl, cycloalkylmethyl, benzyl, 4-methoxybenzyl, halobenzyl, (1-naphthyl)methyl, (2-naphthyl)methyl, (4-imidazolyl)methyl, α, α-dimethylbenzyl, 1-benzyloxyethyl, phenethyl, phenoxy, thiophenoxy or anilino; provided if $R_1$ is phenoxy, thiophenoxy or anilino, B is $CH_2$ or CHOH or A is hydrogen; $R_2$ is hydrogen or loweralkyl; $R_3$ is loweralkyl, loweralkenyl, [(alkoxy)alkoxy]loweralkyl, (thioalkoxy)alkyl, benzyl or heterocyclic ring substituted methyl; $R_4$ is loweralkyl, cycloalkylmethyl or benzyl; $R_5$ is vinyl, formyl, hydroxymethyl or hydrogen; $R_7$ is hydrogen or loweralkyl; $R_8$ and $R_9$ are independently selected from OH and NH2; and $R_6$ is hydrogen, loweralkyl, vinyl or arylalkyl; provided that when $R_5$ and $R_7$ are both hydrogen and $R_8$ and $R_9$ are OH, the carbon bearing $R_5$ is of a "R" configuration and the carbon bearing $R_6$ is of a "S" configuration; or pharmaceutically acceptable salts or esters thereof.

The chiral centers of the compounds of the invention may have either the "R" or "S" configuration but preferably have an "S" configuration except where noted. The terms "S" and "R" configuration are as defined by the IUPAC 1974 Recommendations for Section E, Fundamental Stereochemistry, Pure Appl. Chem. (1976) 45, 13–30.

The term "N-protecting group" or "N-protected" as used herein refers to those groups intended to protect nitrogen atoms against undesirable reactions during synthetic procedures or to prevent the attack of exopeptidases on the final compounds or to increase the solubility of the final compounds and includes but is not limited to acyl, acetyl, pivaloyl, t-butylacetyl, t-butyloxycarbonyl(Boc), benzyloxycarbonyl (Cbz)or benzoyl groups or an L- or D- aminoacyl residue, which may itself be N-protected similarly.

The term "loweralkyl" as used herein refers to straight or branched chain alkyl radicals containing from 1 to 6 carbon atoms including but not limited to methyl, ethyl, n-propyl, iso-propyl, n-butyl, iso-butyl, sec-butyl, n-pentyl, 1-methylbutyl, 2,2-dimethylbutyl, 2-methylpentyl, 2,2-dimethylpropyl, n-hexyl and the like.

The term "loweralkenyl" as used herein refers to a loweralkyl radical which contains at least one carbon-carbon double bond.

The term "arylalkyl" as used herein refers to an unsubstituted or substituted aromatic ring appended to an alkyl radical including but not limited to benzyl, 1- and 2-naphthylmethyl, halobenzyl and alkoxybenzyl.

The term "aminoalkyl" as used herein refers to —NH$_2$ appended to a loweralkyl radical.

The term "cyanoalkyl" as used herein refers to —CN appended to a loweralkyl radical.

The term "hydroxyalkyl" as used herein refers to —OH appended to a loweralkyl radical.

The term "alkylamino" as used herein refers to a loweralkyl radical appended to an NH radical.

The term "cycloalkyl" as used herein refers to an aliphatic ring having 4 to 7 carbon atoms.

The term "cycloalkylmethyl" as used herein refers to an cycloalkyl group appended to a methyl radical, including but not limited to cyclohexylmethyl.

The term "aryl" as used herein refers to a substituted or unsubstituted aromatic ring including but not limited to phenyl, naphthyl, halophenyl and alkoxyphenyl.

The terms "alkoxy" and "thioalkoxy" as used herein refer to $R_{14}O$— and $R_{14}S$—, respectively, wherein $R_{14}$ is a loweralkyl group.

The term "alkenyloxy" as used herein refers to $R_{15}O$ wherein $R_{15}$ is an unsaturated alkyl group.

The term "hydroxyalkoxy" as used herein refers to —OH appended to an alkoxy radical.

The term "dihydroxyalkoxy" as used herein refers to an alkoxy radical which is disubstituted with —OH radicals.

The term "arylalkoxy" as used herein refers to an aryl appended to an alkoxy radical.

The term "arylalkoxyalkyl" as used herein refers to an aryalkoxy appended to a loweralkyl radical.

The term "(thioalkoxy)alkyl" as used herein refers to thioalkoxy appended to a loweralkyl radical.

The term "dialkylamino" as used herein refers to —NR$_{16}$R$_{17}$ wherein R$_{16}$ and R$_{17}$ are independently selected from loweralkyl groups.

The term "[(alkoxy)alkoxy]alkyl" refers to an alkoxy group appended to an alkoxy group which is pended to a loweralkyl radical.

The term "(hydroxyalkyl)(alkyl)amino" as used herein refers to —NR$_{18}$R$_{19}$ wherein R$_{18}$ is hydroxyalkyl and R$_{19}$ is loweralkyl.

The term "N-protected aminoalkyl" as used herein refers to NHR$_{20}$ which is appended to a loweralkyl group, wherein R$_{20}$ is an N protecting group.

The term "alkylaminoalkyl" as used herein refers to NHR$_{21}$ appended to a loweralkyl radical, wherein R$_{21}$ is a loweralkyl group.

The term "(N-protected)(alkyl)aminoalkyl" as used herein refers to NR$_{20}$R$_{21}$, which is appended to a loweralkyl radical, wherein R$_{20}$ and R$_{21}$ are as defined above.

The term "dialkylaminoalkyl" as used herein refers to NR$_{22}$R$_{23}$ is appended to a loweralkyl radical wherein R$_{22}$ and R$_{23}$ are independently selected from loweralkyl.

The term "(heterocyclic)alkyl" as used herein refers to a heterocyclic group appended to a loweralkyl radical, including but not limited to imidazolylalkyl.

The term "O-protecting group" as used herein refers to a substituent which protects hydroxyl groups and includes but is not limited to substituted methyl ethers, for example, methoxymethyl, benzyloxymethyl, 2-methoxyethoxymethyl, 2-(trimethylsilyl)ethoxymethyl and tehahydropyranyl; substituted ethyl ethers, for example, 2,2,2-trichloroethyl, t-butyl, benzyl and triphenylmethyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates.

The term "heterocyclic ring" or "heterocyclic" as used herein refers to any 5-, 6-, 9- or 10- membered ring containing from one to three heteroatoms selected from the group consisting of nitrogen, oxygen, and sulfur; having various degrees of unsaturation; wherein the nitrogen and sulfur heteroatoms may optionally be oxidized; wherein the nitrogen heteroatom may optionally be quaternized; and including any bicyclic group in which any of the above heterocyclic rings is fused to a benzene ring. Heterocyclic in which nitrogen is the heteroatom are preferred. Fully saturated heterocyclics are also preferred. Preferred heterocyclics are: pyrryl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl and benzothienyl.

Saturated heterocyclics may be unsubstituted or monosubstituted with hydroxy, oxo, amino, alkylamino, dialkylamino or loweralkyl. Unsaturated heterocyclics may be unsubstituted or monosubstituted with hydroxy, amino, alkylamino, dialkylamino or loweralkyl.

The most preferred heterocyclics are as follows:

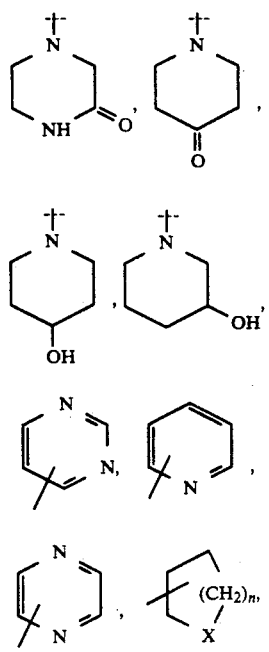

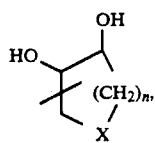

wherein n is 1 or 2 and X is N, NH, O, S, provided that X is the point of connection only when X is N,

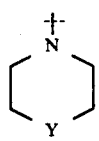

wherein Y is NH, N-loweralkyl, O, S, or $SO_2$, or

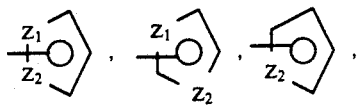

wherein $Z_1$ is N, O, or S and not the point of connection and $Z_2$ is N when it is the point of connection and NH, O or S when it is not the point of connection.

The terms "Ala", "His", "Leu", "Phe", "Tyr", "Cys", "Gly", "Lys", "Sar" and "Pro" as used herein refer to alanine, histidine, leucine, phenylalanine, tyrosine, cysteine, glycine, lysine, sarcosine and proline, respectively.

Most of the compounds of the invention may be made as shown in Scheme I. The amino diol intermediate 5 represents a transition state mimic for the Leu-Val scissile bond of the renin substrate, angiotensinogen. Incorporation of this amine into the angiotensinogen sequence in place of Leu-Val-Ile Protein provides potent inhibitors of human renin. For example, acylation of amine 5 with an acyl-Phe-His OH residue or other appropriately modified amino acid derivatives produces small peptide analogues which are potent renin inhibitors.

SCHEME I

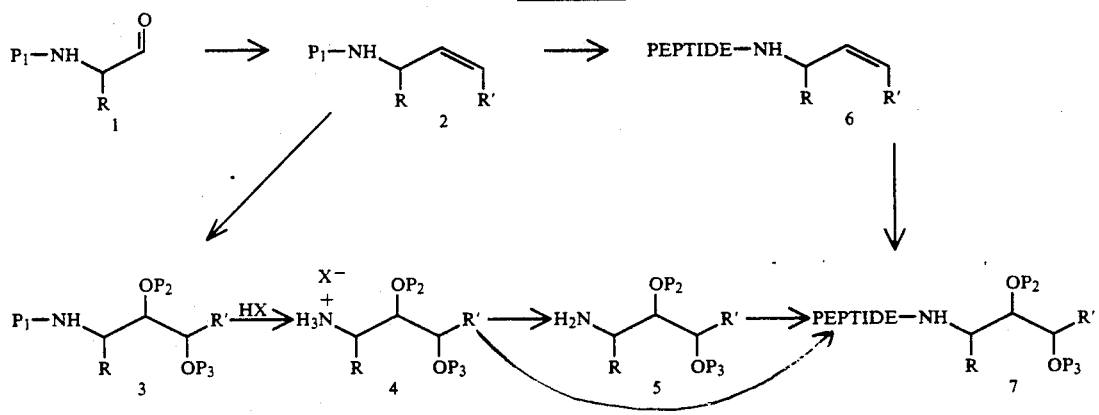

$P_1$ is an N-protecting group; $P_2$ and $P_3$ are independently selected from hydrogen or an O-protecting group.
R is loweralkyl, cycloalkylmethyl or benzyl.
R' is hydrogen, loweralkyl, vinyl or arylalkyl.
HX is an acid.

More particularly, the process shown in Scheme I discloses an N-protected aminoaldehyde 1 ($P_1$ is an N-protecting group) which is treated with an ylide to give the corresponding allylic amine 2. Oxidation gives diol 3 ($P_2$ and $P_3$ are both hydrogen), N-deprotection gives 4; and free-basing gives amine 5. Either intermediate 4 or 5 can be converted to 7 by standard peptide coupling methods. The same sequence (3–7) can be carried out with hydroxy protecting groups present (where $P_2$ and/or $P_3$ are O-protecting groups), the final step then being O-deprotection. Alternatively, allylic amine 2 may be N-deprotected, peptide coupled using standard methods to give 6, and then oxidized to give the desired peptide diols 7.

The protected aminodiol fragment may be alternatively prepared as shown in Scheme II. Aldehyde 9 (prepared, for example, by oxidation of alcohol 8) is converted to its cyanohydrin 10. Addition of an organometallic reagent (such as a Grignard reagent) and acidic workup provides ketone 12. Reduction of ketone 12 then provides the desired protected aminodiol 13.

hours. Evaporation provided a residue which was partitioned between ethyl acetate (30 mL) and 0.1M H3PO4 (10 mL). The organic phase was washed with brine (10 mL), saturated NaHCO3 (10 mL), and brine (10 mL).

SCHEME II

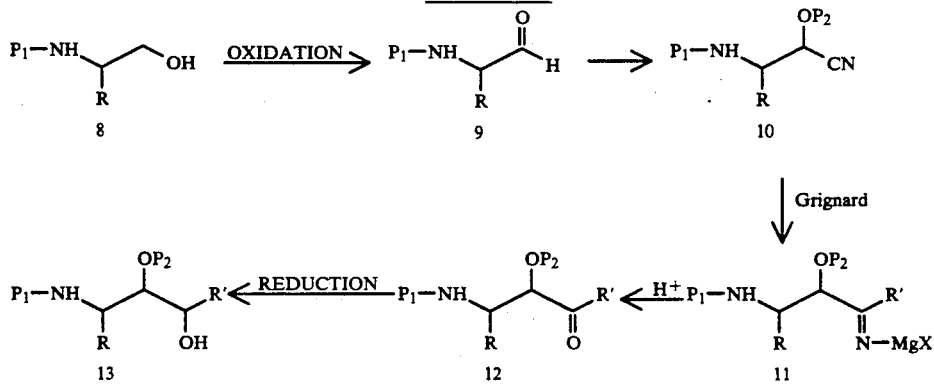

P1, P2, R and R' are as defined for Scheme I, except that R' cannot be hydrogen.

The following Examples will to further illustrate preparation of the novel compounds of the invention.

EXAMPLES 1

2(S)-t-Butyloxycarbonylamino-1-cyclohexylbut-3-ene

A 0° C. solution of potassium hexamethyldisilazide (22.9 mmol in 115 mL of 5:1, tetrahydrofuran (THF): dimethyl sulfoxide (DMSO) was added dropwise to triphenylmethylphosphonium iodide (24.81 mmol). After stirring at 0° C. for 1 hour, the solution was cooled to −78° C. and a solution of Boc-cyclohexylalaninal [4.90 g, 19.08 mmol, prepared by Swern oxidation (Mancuso, A. J.; Huang,, S. -L.; and Swern, D., J. Org. Chem. 1978, 43, 2480) of Boc cyclohexylalaninol] in dry THF (95 mL) was added. After stirring at −78° C. for 1 hour, the mixture was allowed to warm to room temperature. The reaction mixture was quenched with aqueous ammonium chloride and extracted with ether (2×300 mL). The combined organic phase was washed with 10% HCl (200 mL), saturated NaHSO3 (2×200 mL), H2O (2×200 mL), saturated NaHCO3 (2×200 mL), and brine (200 mL), dried (MgSO4), filtered, and evaporated. The residue was purified by chromatography (40 m SiO2; ether:hexane, 15:85) to give the desired compound in 60% yield. Mass spectrum: $(M+H)^+ = 254$.

EXAMPLE 2

Boc-Phe-Ala Amide of (2S)-Amino-1-cyclohexylbut-3-ene

The resultant compound of Example 1 (310 mg, 1.22 mmol) was dissolved in 1M anhydrous HCl in anhydrous methanol (35 mL). After 22 hours, the solvent was evaporated to give 230 mg (99%) of the corresponding amine hydrochloride which was used without further purification.

To a stirred −13° C. solution of Boc-Phe Ala (408 mg, 1.21 mmol) in dry THF (8 mL) containing N-methylmorpholine (122 mg, 1.21 mmol) was added isobutyl chloroformate (165 mg, 1.21 mmol) dropwise. After 3 minutes, a −13° C. solution of the above amine hydrochloride (230 mg, 1.21 mmol) in 1:1, THF:dimethyl formamide (DMF) (4 mL) containing N-methylmorpholine (122 mg) was added dropwise. The mixture was warmed to room temperature for 2 hours. Evaporation provided a residue which was partitioned between ethyl acetate (30 mL) and 0.1M H3PO4 (10 mL). The organic phase was washed with brine (10 mL), saturated NaHCO3 (10 mL), and brine (10 mL). Drying, filtering, evaporating, and chromatographing (55 g SiO2; 95:5, CH2C12:CH3OH) ave the desired compound (462 mg, 81%).

EXAMPLE 3

Boc-Phe-Ala Amide of 3(S)-Amino-4-cyclohexyl-1,2(R,S)-dihydroxybutane

To a stirred solution of the resultant compound of Example 2 (100 mg, 0.212 mmol) in THF (5 mL) were added OsO4 solution (0.065 mL of a 2.5 W/V% solution in t-butanol) and N-methylmorpholine N-oxide (57 mg, 0.424 mmol) sequentially. After 4.5 hours, brine (10 mL) was added, and the mixture was extracted with ether (4×8 mL). The combined organic phase was washed with 10% Na2SO3 (3×6 mL), 0.1M H3PO4 (5 mL), and brine (5 mL). Drying, filtering, and evaporating provided the desired product (97 mg, 91%). Mass spectrum: $M^+ = 505$.

EXAMPLE 4

3(S)-t-Butyloxycarbonylamino-4cyclohexyl-1,2(R,S)-dihydroxybutane

To a stirred solution of 2(S)-t-butyloxycarbonylamino-1-cyclohexylbut 3-ene (1.00 g, 3.95 mmol) in THF (20 mL) were added OsO4 solution (1.2 mL of a 2.5 W/V% solution in t-butanol) and N-methylmorpholine N-oxide (1.07 g, 7.90 mmol). After 24 hours, the mixture was partitioned between ether (50 mL) and brine (25 mL). The layers were separated, and the organic phase was extracted with ether (3×25 mL). The combined organic phase was washed with 10% Na2SO3 (4×10 mL), 1.0M H3PO4 (2×8 mL), and brine (15 mL). Drying and evaporating provided the desired product as an oil (1.14 g, 100%). 'H NMR shows a 1:1 mixture of diastereomers (NH 4.43 and 4.56 ppm).

EXAMPLE 5

Boc-Phe-His Amides of 3(S)-Amino-4-cyclohexyl-2(R,S)-hydroxy-1-t-butyldimethylsilyloxybutane The resultant compound of Example 4 (1.10 3.82 mmol) was treated with anhydrous 1M HCl/CH3OH (80 mL) for 16 hours at which time evaporation and drying provided the corresponding amine hydrochloride (0.85 g, 100%)

To a suspension of the above hydrochloride salt (344 mg, 1.54 mmol) and imidazole (105 mg) in dichloromethane (15 mL) were added triethylamine (156 mg) and t-butyldimethylsilyl chloride (232 mg). The solvent was evaporated after 31 hours, and the residue was then re-dissolved in anhydrous dimethylformamide (DMF, 15 mL). Boc-Phe-His (619 mg) and 1-hydroxybenzotriazole (HOBT, 312 mg) were then added. After cooling the stirred solution to $-23°$ C., 1,3-dicyclohexylcarbodiimide (DCC, 318 mg) was added. The mixture was warmed to room temperature 3 hours later. After 13 hours the solvent was evaporated in vacuo, and the residue was dissolved in ethyl acetate (40 mL), filtered, washed with saturated $NaHCO_3$ (2×10 mL) and brine (10 mL), and dried ($Na_2SO_4$). Filtration and evaporation provided a residue which was chromatographed on silica gel eluting with dichloromethane/methanol mixtures to give 441 mg (42%) of the desired product. Mass spectrum: $(M+H)^+ = 686$.

Anal. calcd. for $C_{36}H_{59}N_5O_6Si$: C, 63.0; H, 8.7; N, 10.2. Found: C, 62.8; H, 9.0; N, 9.9.

EXAMPLE 6

Boc-Phe-His Amides of
3(S)-Amino-4-cyclohexyl-1,2(R)-dihydroxybutane

To a stirred solution of the resultant product of Example 5 (200 mg, 0.291 mmol) in anhydrous THF (5 mL) at 0° C. was added tetrabutylammonium fluoride (0.58 mL of a 1M solution in THF). The solution was warmed to room temperature for 4 hours and then evaporated. The residue was dissolved in chloroform and washed with water (3X) and brine (1X). Drying and evaporating provided a gum which was treated with hot ethyl acetate (8 mL). Cooling and filtration provided 25 mg of the desired material. Mass spectrum: $(M+H)^+ = 572$.

Anal. Calcd for $C_{30}H_{45}N_5O_6$ $1/2H_2O$: C 62.1; H, 8.0; N, 12.1. Found: C, 62.4; H, 8.2; N, 12.0.

EXAMPLE 7

(4S)-2,8-Dimethyl-4-[(toluenesulfonyl)amino]-5-nonanone

To a stirred $-78°$ C. solution of toluenesulfonyl (Ts)-Leu (15 g, 53 mmol) in dry THF (240 mL) was added butyl lithium (57.8 mL of a 0.91M solution in hexane) followed 15 minutes later by isopentyl magnesium bromide (185 mL of a 0.8M solution in THF). The mixture was heated at reflux for 3 days, then cooled and poured into 0° C. 1M HCl (500 mL). The layers were separated and the aqueous phase was extracted with ether (3×150 mL). The combined organic layers were washed with saturated $NaHCO_3$ (2×150 mL) and brine (150 mL), Drying and evaporating provided a residue which was chromatographed on silica gel to give 7.43 (41%) of the desired product. Mass spectrum: $(M+H)^+ = 340$.

Anal. calcd. for $C_{18}H_{29}NO_3S$: C, 63.7; H, 8.6; N, 4.1. Found: C, 64.0; H, 8.6; N, 4.1.

EXAMPLE 8

(4S)-2,8-Dimethyl-5-hydroxy-4-[(toluenesulfonyl)amino]-5-vinylnonane

To a stirred 0° C. solution of the resultant compound of Example 7 (79 mg, 0.23 mmol) in dry THF (8 mL) was added vinyl magnesium bromide (1.5 mL of a 1.0M solution in THF) dropwise. The mixture was warmed (room temperature, 10 hours), quenched (8 mL $H_2O + 2$ mL brine), acidified with 0.1M $H_3PO_4$ (pH=7), and extracted with ether (3×4 mL). The combined ether phase was washed (4 mL brine), dried ($Na_2SO_4$), filtered, and evaporated to give 81 mg (95%) of the desired product as a 4:1 mixture of diastereomers.

EXAMPLE 9

Boc-Phe-Ala Amide of
(4S)-Amino-2,8-dimethyl-5-hydroxy-5-vinylnonane

To a solution of the resultant compound of Example 8 (400 mg, 1.09 mmol) in liquid ammonia (80 mL) was added sodium (150 mg, 6.5 mmol). After 6 hours the ammonia was allowed to slowly evaporate under a stream of nitrogen. Benzene (50 mL) and 1:1, ethanol:-water (20 mL) were added with stirring. The layers were separated, and the aqueous phase was extracted with ether. The combined organic phase was dried ($Na_2SO_4$), filtered, and evaporated to give 85 mg (37%) of the desired product.

Following the procedure of Example 2, but replacing the amine hydrochloride and N-methylmorpholine with the above resultant product, gave the desired major diastereomer in 35% yield after chromatography. FAB mass spectrum: $(M+K)^+ = 570$.

Anal. calcd. for $C_{30}H_{49}N_3O_5$: % C, 67.8; H, 9.3; N, 7.9. Found: C, 67.7; H, 9.6; N, 7.3.

EXAMPLE 10

Boc-Phe-Ala Amide of
(3S)-Amino-2-hydroxy-2-isopentyl-5-methylhexanal

Following the procedure of Example 3 with the resultant compound of Example 9 except replacing N-methylmorpholine N-oxide with aqueous $NaIO_4$ gave the desired compound.

EXAMPLE 11

Boc-Phe-Ala Amide of
3-Amino-1,2-dihydroxy-2-isopentyl-5-methylhexane

Treatment of the resultant compound of Example 10 with one equivalent of $NaBH_4$ in methanol provided the desired compound after aqueous work-up.

EXAMPLE 12

Boc-Phe-Ala Amide of
3-Amino-1,2-dihydroxy-2-isopentyl-5-methylhexane

Scale up of the procedure of Example 8 led to the isolation of the minor diastereomer pure after chromatography. Treatment as in Examples 9, 10, and 11 provided the desired isomer of the resultant product of Example 11.

EXAMPLE 13

2(S)-t-Butyloxycarbonylamino-1-cyclohexyl-6-methylhept-3-ene

To a stirred $-78°$ C. solution of Boc-cyclohexylalanine methyl ester (40 g, 140 mmol) in anhydrous toluene (250 mL) was added diisobutylaluminum hydride (130M %, 1.5M solution in toluene, 121.4 mL) at a rate to keep the internal temperature below $-60°$ C. After stirring for an additional 20 minutes at $-78°$ C., the aldehyde solution is used immediately as described below.

To a potassium hydride (35% dispersion in oil, 32.09 g) suspension in a 0° C. mixture of anhydrous THF/DMSO (1000 mL/200 mL) under dry $N_2$ was added 1,1,1,3,3,3-hexamethyldisilazane (209M %, 49.07 g) dropwise. After stirring at 0° C. for 1 hour, the resulting solution was added via cannula to a 0° C. flask containing isopentyltriphenylphosphonium bromide (209 M %, 125.66 g). The mixture was stirred vigorously for 1 hour at which time it was cooled to −78° C. The −78° C. aldehyde solution prepared above was then added via cannula. After stirring at −78° C. for 15 minutes, the mixture was allowed to slowly warm to room temperature and then heated to 40° C. for 12 hours. The mixture was then cooled to room temperature and quenched with methanol (7.65 mL) followed by aqueous Rochelle salts (100 mL saturated solution and 500 mL $H_2O$). The mixture was then extracted with ethyl acetate (2x). The combined extracts were washed with water and brine. Drying ($MgSO_4$) and evaporating provided crude alkene which was chromatographed on silica gel (ether/hexane) to give 16.5 g (38%) of the desired compound as an 85:15 mixture of cis:trans isomers. Mp=53°-55° C. Mass spectrum: $M^+$ =309.

Anal. calcd. for $C_{19}H_{35}NO_2$: C, 73.7; H, 11.4; N, 4.5. Found: C, 73.8; H, 11.4; N, 4.5.

EXAMPLE 14

2(S)-t-Butyloxycarbonylamino-1-cyclohexyl-3,4-dihydroxy-6-methylheptane: The 3(R)4(S), 3(S)4(S), 3(R)4(R), and 3(S)4(R) Diastereomers To a solution of the resultant compound of Example 13 (8.50, 27.5 mmol) in dry THF (150 mL) were added $OsO_4$ (2.8 mL of a 2.5% solution in t-butanol and N-methylmorpholine N-oxide (9.28 g, 68.7 mmol). After 4 days the mixture was partitioned between ether (200 mL) and brine (100 mL). The aqueous layer was back-extracted with ether (2×100 mL), and the combined organic phase was washed with 10% $Na_2SO_3$, 0.1M $H_3PO_4$, and brine. Drying ($MgSO_4$) and evaporating provided a residue (10.81 g) which was chromatographed on silica gel to elute a 60% yield of the 4 diols in the following order.

3(R),4(S) Mass spectrum: $(M+H)^+$ =344. Anal. calcd. for $C_{19}H_{37}NO_4$: C, 66.4; H, 10.9; N, 4.1. Found: C, 66.4; H, 10.8; N, 3.9.

3(S),4(S) Mass spectrum: $(M+H)^+$ =344. Anal. calcd. for $C_{19}H_{37}NO_4$: C, 66.4; H, 10.9; N, 5.1. Found: C, 66.4; H, 11.1; N, 4.0.

3(R),4(R) Mass spectrum: $(M+H)^+$ =344.

3(S),4(R) Mass spectrum: $(M+H)^+$ =344. Anal. calcd. for $C_{19}H_{37}NO_4$: C, 66.4; H, 10.9; N, 4.1. Found: C, 66.0; H, 10.7; N, 4.0.

EXAMPLE 15

Boc-Phe-His Amide of 2(S)-Amino-1-cyclohexyl-3(R),4(S)-dihydroxy-6-methylheptane The 3(R),4(S) diastereomer of Example 14 was deprotected with HCl/methanol, and the resulting product was coupled to Boc-Phe-His using 1-hydroxybenzotriazole and 1,3-dicyclohexylcarbodiimide according to the procedure of Example 5. The desired product was obtained in 40–60% yield. Mass spectrum: $(M+H)^+$ =628.

Anal. calcd. for $C_{34}H_{53}N_5O_6 H_2O$: C, 63.2; H, 8.6; N, 10.8. Found: C, 63.2; H, 8.4; N, 10.5.

EXAMPLE 16

Boc-Phe-His Amide of 2(S)-Amino-1-cyclohexyl-3(S),4(S)-dihydroxy-6-methylheptane Following the procedure of Example 15, but replacing the 3(R),4(S) diastereomer with the 3(S),4(S) diastereomer gave the desired compound. Mass spectrum: $(M+H)^+$ =628.

Anal. calcd. for $C_{34}H_{53}N_5O_6 \frac{1}{2}H_2O$: C, 64.1; H, 8.6; N, 11.0. Found: C, 64.0; H, 8.6; N, 10.6.

EXAMPLE 17

Boc-Phe-His Amide of 2(S)-Amino-1-cyclohexyl-3(R),4(R)-dihydroxy-6-methylheptane Following the procedure of Example 15, but replacing the 3(R),4(S) diastereomer with the 3(R),4(R) diastereomer gave the desired compound. Mass spectrum: $(M+H)^+$ =628.

Anal. calcd. for $C_{34}H_{53}N_5O_6 H_2$): C, 63.2, H, 8.6; N, 10.8. Found: C, 63.1H, 8.5; N, 10.7.

EXAMPLE 18

Boc-Phe-His Amide of 2(S)-Amino-1-cyclohexyl-3(S),4(R)-dihydroxy-6-methylheptane Following the procedure of Example 15, bit replacing the 3(R),4(S) diastereomer with the 3(S),4(R) diastereomer gave the desired compound. Mass spectrum: $(M+H)^+$ =628.

Anal. calcd. for $C_{34}H_{53}N_5O_6 \frac{3}{4}H_2O$; C, 63.7; H, 8.6; N, 10.9. Found: C, 63.8; H, 8.8; N, 10.7.

EXAMPLE 19

A.

4(S)-t-Butyloxycarbonylamino-5-cyclohexyl-3(R,S)-hydroxy-1-pentene

To a stirred −78° C. solution of Boc-cyclohexylalanine methyl ester (10.2 g, 35.8 mmol) in dry toluene (60 mL) was added diisobutylaluminum hydride (34 mL of a 1.5M solution in toluene) After 30 minutes, vinyl magnesium bromide (108 mL of 1M solution in THF) was added. After stirring for 15 hours at 0° C., the mixture was carefully quenched with methanol, treated with Rochelle salts (22 mL of saturated aqueous solution in 140 mL $H_2O$), and filtered. After extracting the solids 5 times with ethyl acetate, the extracts and filtrate were combined and the organic phase was washed with brine, dried, filtered, and evaporated to an oil (10.2 g). Chromatography on silica gel eluting with hexane/ethyl acetate mixtures provided 6.1 g (60%) of the desired product.

Anal. calcd. for $C_{16}H_{29}NO_3$ 1/4$H_2O$: C, 66.8; H, 10.3; N, 4.9. Found: C, 66.9; H, 10.2; N, 4.7.

B.

4(S)-Cyclohexylmethyl-5(R,S)-vinyl-2-oxazolidinone

The resultant product of Example 19A (2.80 g, 9.88 mmol) in dry dimethylformamide (DMF) (50 mL) was added to a stirred suspension of NaH (593 mg of a 60% dispersion in oil, 14.8 mmol, hexane washed) in dry DMF (50 mL). After 3 hours, the mixture was quenched (750 mL water+100 mL brine) and extracted with ether (5×100 mL). The combined organic phase was washed with brine (3×50 mL), dried ($MgSO_4$), filtered, and evaporated to an oil 2.23 g. The NMR spectrum of the crude product revealed an 82:18 mixture of 5 S:5 R diastereomers. Silica gel chromatography gave 80% recovery of pure diastereomers. 5 S:

Anal. calcd. for $C_{12}H_{19}NO_2$: C, 68.9; H, 9.1; N, 6.7. Found: 68.4; H, 9.2; N, 6.5. Mass, spectrum: $(M+1)^+ = 210$. 5 R: Mass spectrum: $(M+1)^+ = 210$.

C.
5(R)-Carboxy-4-(S)-cyclohexylmethyl-2-oxazolidinone

To a solution of the compound from Example 19B (1 g, 4.78 mmol) dissolved in 16 mL of benzene and 3 mL of acetic acid was added a solution of 3.01 of potassium permanganate in 16 mL of water. The resultant two-phase mixture was vigorously stirred and treated by portionwise addition with 153 mg of tetrabutylammonium bromide. After stirring for 2 hours at room temperature, the mixture was quenched with aqueous sodium bisulfite, acidified to pH=3, and extracted with ethyl acetate. Drying and evaporating gave the desired product as an oil in 59% yield.

D.
4(S)-Cyclohesylmethyl-5(R)-[3-(3-hydroxypentyl)]-2-oxazolidinone

To a solution of the compound from Example 19C dissolved in tetrahydrofuran and cooled to −78° C. was added 3.5 equivalents of ethyl magnesium bromide. After stirring at −78° C. for 1.5 hours and at room temperature for 1 hour, the reaction mixture was quenched with water and extracted with ether. The dried ethereal extract was evaporated to afford a 73% yield of product.

E.
2(S)-Amino-1-cyclohexyl-3(R)-3,4-dihydroxy-4-ethylhexane

A solution of the compound from Example 19D (1.69 mmol) and barium hydroxide octahydrate (3.38 mmol) in dioxane (60 mL) and water (40 mL) was heated at reflux under $N_2$ for 21 hours. The solid barium carbonate was filtered and the filtrate was partially evaporated. The residue was diluted with water and the resulting solution was extracted with ether. The organic extract was washed with brine solution, dried over $MgSO_4$, and evaporated to give the desired product in 76% yield.

F. Boc-Phe-His Amide of 2(S)-Amino-1-cyclohexyl-3(R)-3,4-dihydroxy-4-ethylhexane The resultant product of Example 19E was coupled to Boc-Phe-His using 1-hydroxybenzotriazole and 1,3-dicyclohexylcarbodiimide according to the procedure of Example 5 to give the desired product in 55% yield.

EXAMPLE 20
Boc-His Amide of 2(S)-Amino-1-cyclohexyl-3(R),4(S)-dihydroxy-6-methylheptane The procedure of Example 15 was followed except Boc-Phe-His was replaced with Boc-His. Mass spectrum: $(M)^+ = 480$.

Anal calcd. for $C_{25}H_{44}N_4O_5 \cdot \frac{3}{4}H_2O$: C, 60.8; H, 9.1; N, 11.3. Found: C, 60.9; H, 9.2; N, 11.0.

EXAMPLE 21
TBA-CHA-His Amide of 2(S)-Amino-1-cyclohexyl-3(R),4(S)-dihydroxy-6-methylheptane The resultant compound of Example 20 was deprotected with HCl/methanol, and the resulting product was coupled to t-butylacetyl-cyclohexylalanine (TBA-CHA) using the DCC/HOBT method of Example 5. HRMS calcd. for $C_{35}H_{61}N_5O_5$. $(M+H)$ 632.4751. Found: 632.4759.

EXAMPLE 22
Ethoxycarbonyl-(OCH$_3$)Tyr-His Amide of 2(S)-Amino-1-cyclohexyl-3(R),4(S)-dihydroxy-6-methylheptane Using the procedure of Example 21, but replacing TBA-CHA with ethoxycarbonyl-(OCH$_3$)Tyr-His gave the desired compound. Mass spectrum: $(M+H)^+ = 630$.

EXAMPLE 23
Acetyl-N-methylPhe-His Amide of 2(S)-Amino-1-cyclohexyl-3(R),4(S)-dihydroxy-6-methylheptane Using the procedure of Example 21, but replacing TBA-CHA with acetyl-N-methylPhe gave the desired compound Mass spectrum: $M^+ = 583$.

EXAMPLE 24
Ac-Pl-His Amide of 2(S)-Amino-1-cyclohexyl-3(R),4(S)-dihydroxy-6-methylheptane Using the procedure of Example 21, but replacing TBA-CHA with 0-acetyl-L-3-phenyllactic acid (Ac-Pl-OH) gave the desired compound. HRMS calcd. for $C_{31}H_{46}N_4O_6$, $(M+H)$ 571.3495. Found: 571.3489.

EXAMPLE 25
Pl-His Amide of 2(S)-Amino-1-cyclohexyl-3(R),4(S)-dihydroxy-6-methylheptane The resultant compound of Example 24 (37.4 mg, 0.065 mmol) in MeOH at 0° C. was treated with $K_2CO_3$ (9.1 mg, 0.065 mmol) for 30 minutes at 0° C. Evaporation provided a residue which was partitioned between ethyl acetate and water. The organic phase was washed (brine), dried ($MgSO_4$), and evaporated to give the desired compound (32 mg, 93%). Mass spectrum: $(M+H)^+ = 529$.

Anal calcd. for $C_{31}H_{46}N_4O_6 \cdot \frac{1}{2}H_2O$ C, 64.8; H, 8.4; N, 10.4. Found: C, 64.6; H, 8.3; N, 10.1.

EXAMPLE 26
Boc-1-Nal-His Amide of 2(S)-Amino-1-cyclohexyl-3(R),4(S)-dihydroxy-6-methyl-heptane Using the procedure of Example 21, but replacing TBA-CHA with Boc-1-naphthylalanine (Boc-1-Nal) provided the desired compound. Mass spectrum: $(M+H)^+ = 678$.

EXAMPLE 27

Dba-His Amide of 2(S)-Amino-1-cyclohexyl-3(R),4(S)-dihydroxy-6-methylheptane

Using the procedure of Example 21, but replacing TBA-CHA with 2,2 dibenzylacetic acid (Dba-OH) ave the desired compound. HRMS calcd. for $C_{36}H_{50}N_4O_4$, (M+H) 603.3910. Found: 603.3899.

EXAMPLE 28

Pp-His Amide of 2(S)-Amino-1-cyclohexyl-3(R),4(S)-dihydroxy-6-methylheptane

Using the procedure of Example 21, but replacing TBA-CHA with 3-phenyl-propionic acid (Pp-OH) gave the desired compound. Mass spectrum: $(M+H)^+ = 513$.

Anal. calcd. for $C_{29}H_{44}N_4O_4 \cdot \frac{1}{2} H_2O$: C, 66.8; H, 8.7., N, 10.7. Found: C, 66.6; H, 8.8; N, 10.5.

EXAMPLE 29

Ethoxycarbonyl-Phe-His Amide of 2(S)-Amino-1-cyclohexyl-3(R),4(S)-dihydroxy-6-ethylheptane Using the procedure of Example 21, but replacing TBA-CHA with ethoxycarbonyl-Phe gave the desired product. Mass spectrum: $(M+H)^+ = 600$.

Anal. calcd. for $C_{32}H_{49}N_5O_6 \cdot \frac{1}{2}H_2O$: C, 63.1; H, 8.3; N, 11.5. Found: C, 62.8; H, 8.3; N, 11.4.

EXAMPLE 30

Ac-Phe-His Amide of 2(S)-Amino-1-cyclohexyl-3(R),4(S)-dihydroxy-6-methylheptane

Using the procedure of Example 21, but replacing TBA-CHA with acetyl(Ac)-Phe gave the desired duct. Mass spectrum: $(M+H)^+ = 570$.

Anal calcd. for $C_{31}H_{47}N_5O_5 \cdot \frac{1}{2}H_2O$: C, 64.3; H, 8.2; N, 12.1. Found: C, 64.2; H, 8.3; N, 12.0.

EXAMPLE 31

Boc-Leu-His Amide of 2(S)-Amino-1-cyclohexyl-3(R),4(S)-dihydroxy-6-methylheptane Using the procedure of Example 21, but replacing TBA-CHA with Boc-Leu gave the desired product. Mass spectrum: $(M+H)^+ = 594$.

Anal. calcd. for $C_{31}H_{55}N_5O_6 \cdot \frac{1}{2}H_2O$: C, 61.8; H, 9.4; N, 11.6. Found: C, 61.8; H, 9.3; N, 11.6.

EXAMPLE 32

Tbac-Phe-His Amide of 2(S)-Amino-1-cyclohexyl-3(R),4(S)-dihydroxy-6-methylheptane Using the procedure of Example 21, but replacing TBA-CHA with t-butyl-aminocarbonyl-Phe (Tbac-Phe) gave the desired product. Exact mass calcd for $C_{34}H_{55}N_6O_5$: 627.4233. Found: 627.4226.

EXAMPLE 33

Boc-Phe-Ala Amide of 2(S)-Amino-1-cyclohexyl-3(R),4(S)-dihydroxy-6-methylheptane Using the procedure of 2, but replacing the resultant compound of Example 1 with the 3(R),4(S) diastereomer of Example 14 gave the desired compound. Mass spectrum: $(M H)^+ = 560$.

Anal. calcd. for $C_{31}H_{51}N_3O_6$: C, C, 66.3; H, 9.1; N, 7.5. Found: C, 66.0; H, 9.2; N, 7.3.

EXAMPLE 34

Boc-Phe-Phe Amide of 2(S)-Amino-1-cyclohexyl-3(R),4(S)-dihydroxy-6-methylheptane Using the procedure of Example 33, but replacing Boc Phe-Ala with Boc-Phe-Phe, gave the desired product. Mass spectrum: $(M+H)^+ = 638$.

Anal. calcd. for $C_{37}H_{55}N_3O_6$: C, 69.7; H, 8.7; N, 6.6. Found C, 69.4; H, 8.8; N, 6.5

EXAMPLE 35

Boc-Phe-PAla Amide of 2(S)-Amino-1-cyclohexyl-3(R),4(S)-dihydroxy-6-methylheptane Using the procedure of Example 33, but replacing Boc-Phe-Ala with Boc-Phe-(3-pyrazoyl)alanine (Boc-Phe-PAla), gave the desired compound. Mass spectrum: $(M+H)^+ = 628$.

Anal. calcd. for $C_{34}H_{53}N_5O_6 \cdot \frac{1}{2}H_2O$: C, 64.1; H, 8.5; N, 11.0. Found: C, 64.1; H, 8.3; N, 11.2.

EXAMPLE 36

Ethoxycarbonyl-Phe-Leu Amide of 2(S)-Amino-1-cyclohexyl-3(R),4(S)-dihydroxy-6-methylheptane Using the procedure of Example 33, but replacing Boc-Phe-Ala with Boc-Phe-Leu, gave the desired compound. Mass spectrum: $(M+H)^+ = 576$.

Anal. calcd. for $C_{32}H_{53}N_3O_6$: C, 66.7; H, 9.3; N, 7.3. Found: C, 66.4; H, 9.5; N, 7.2.

EXAMPLE 37

Boc-Phe-(SCH$_3$)Cys Amide of 2(S)-Amino-1-cyclohexyl-3(R),4(S)-dihydroxy-6-methylheptane Using the procedure of Example 33, but replacing Boc-Phe-Ala with Boc-Phe-(SCH$_3$)Cys, gave the desired compound. Mass spectrum: $(M+H)^+ = 608$.

Anal. calcd. for $C_{32}H_{53}N_3O_6S$: C, 62.8; H, 8.8; N, 6.9. Found: C, 62.8; H, 8.9; N, 6.6.

EXAMPLE 38

Ts-(N Me,N$_{IM}$Bn)-His Amide of 2(S)-Amino-1-cyclohexyl-3(R),4(S)-dihydroxy-6-methylheptane Using the procedure of Example 20, but replacing Boc-His with (N tosyl, N methyl, N imidazole benzyl)-His [Ts-(N Me,N$_{IM}$Bn)-His] (DuVigneau, V.; Behrens, O. K. *J. Biol. Chem.* 1937, 117, 27), gave the desired compound. Mass spectrum: $(M+H)^+ = 639$.

EXAMPLE 39

Ethoxycarbonyl-Phe-MeHis Amide of 2(S)-Amino-1-cyclohexyl-3(R),4(S)-dihydroxy-6-methylheptane To a stirred −78° C. solution of the resultant compound of Example 38 (100 mg, 0.156 mmol) in liquid NH$_3$ (5 mL) and dry tetrahydrofuran (5 mL) was added sodium until a dark green/brown color persisted for 5 minutes. Solid, powdered NH$_4$Cl was then added, and the mixture was evaporated. The residue was suspended in water and extracted several times with chloroform. The combined extracts were dried ($Na_2SO_4$), filtered, and evaporated to give the MeHis amide of 2(S)-amino-1-cyclohexyl-3(R),4(S)-dihydroxy-6-methylheptane. The material was coupled to ethoxycarbonyl-Phe using to DCC/HOBT method described in Example 5 to give the desired product. Mass spectrum: $(M+H)^+ = 614$.

EXAMPLE 40

2(S)-t-Butyloxycarbonylamino-1-cyclohexyl-7-methyloct-3-ene

Using the procedure of Example 13, but replacing isopentyltriphenylphosphonium bromide with isohexyltriphenylphosphonium bromide, gave the desired product.

EXAMPLE 41

2(S)-t-Butyloxycarbonylamino-1-cyclohexyl-3(R),4(S)-dihydroxy-7-methyloctane

Using the procedure of Example 14, but replacing the resultant compound of Example 13 with the resultant compound of Example 40, gave the desired compound.

EXAMPLE 42

Boc-His Amide of 2(S)-Amino1-cyclohexyl-3(R),4(S)-dihydroxy-7-methyloctane

Using the procedure of Example 20, but replacing the 3(R),4(S) diastereomer of Example 14 with the resultant compound of Example 41, gave the desired product. Mass spectrum: $(M+H)^+ = 495$.

Anal. calcd. for $C_{26}H_{46}N_4O_5 \cdot \frac{1}{2}H_2O$: C, 62.0; H, 9.4; N, 11.1. Found: C, 62.2; H, 9.4; N, 10.9.

EXAMPLE 43

TBA-Phe-His Amide of 2(S)-Amino-1-cyclohexyl-3(R),4(S)-dihydroxy-7-methyloctane

Using the procedure of Example 15, but replacing the resultant compound of Example 14 and Boc-Phe-His with the resultant compound of Example 42 and t-butylacetyl(TBA)-Phe gave the desired compound. Mass spectrum: $(M+H)^+ = 640$.

Anal. calcd. for $C_{36}H_{57}N_5O_5 \cdot \frac{2}{3}H_2O$: C, 66.2; H, 9.0; N, 10 7. Found: C, 66.1; H, 9.1; N, 10.6.

EXAMPLE 44

2(S)-t-Butyloxycarbonylamino-1-cyclohexyl-5-methylhex-3-ene

Using the procedure of Example 13, but replacing isopentyltriphenylphosphonium bromide with isobutyltriphenylphosphonium bromide, gave the desired product. Mass spectrum: $M^+ = 295$.

Anal. calcd. for $C_{18}H_{33}NO_2 \cdot \frac{1}{4}H_2O$: C, 72.0; H, 11.3; N, 4.7. Found: 71.7; H, 11.1; N, 4.5.

EXAMPLE 45

2(S)-t-Butyloxycarbonylamino-1-cyclohexyl-3(R),4(S)-dihydroxy-5-methylhexane

Using the procedure of Example 14, but replacing the resultant compound of Example 13 with the resultant compound of Example 44, gave the desired compound.

EXAMPLE 46

Boc-Phe-His Amide of 2(S)-Amino-1-cyclohexyl-3(R),4(S)-dihydroxy-5-methylhexane

Using the procedure of Example 15, but replacing the resultant product of Example 14 with the resultant product of Example 45, gave the desired product. Mass spectrum: $(M+H)^+ = 614$.

EXAMPLE 47

Ethoxycarbonyl-Phe-Leu Amide of 2(S)-Amino-1-cyclohexyl-3(R),4(S)-dihydroxyhexane Following the procedures used to make the resultant compound of Example 36, but replacing isopentyltriphenylphosphonium bromide with propyltriphenylphosphonium bromide, gave the desired product. Mass spectrum: $M^+ = 547$.

Anal. calcd. for $C_{30}H_{49}N_3O_6 \cdot \frac{1}{4}H_2O$: C, 65.2; H, 9.0; N, 7.6. Found: C, 65.0; H, 8.9; N, 7.3.

EXAMPLE 48

Ethoxycarbonyl-Phe-Leu Amide of 2(S)-Amino-1-cyclohexyl-3(R),4(S)-dihydroxy-5-phenylpentane Following the procedures used to make the resultant compound of Example 36, but replacing isopentyltriphenylphosphonium bromide with phenethyltriphenylphosphonium bromide, gave the desired product.

EXAMPLE 49

Boc-Phe-His Amide of 2(S)-Amino-1-cyclohexyl-3(R),4(S)-dihydroxypentane

Following the procedures used to make the resultant compound of Example 15, but replacing isopentyltriphenylphosphonium bromide with ethyltriphenylphosphonium bromide, gave the desired product. Mass spectrum: $(M+H) = 600$.

Anal. calcd. for $C_{32}H_{49}N_5O_6 \cdot \frac{1}{4}H_2O$: C, 63.6; H, 8.3; N, 11.6. Found: C, 63.6; H, 8.3; N, 11.5.

EXAMPLE 50

2(S)-t-Butyloxycarbonylamino-1-cyclohexyl-3(S)-hydroxyhex-5-ene

To a stirred $-78°$ C. solution of Boc-cyclohexylalanine methyl ester (35.0 g, 123 mmol) in anhydrous toluene (200 mL) was added diisobutylaluminum hydride (140 M %, 1.5M solution in toluene, 117 mL) at a rate to the internal temperature below $-60°$ C. After stirring for an additional 20 minutes at $-78°$ C., allyl magnesium chloride (184 mL of a 2.0M solution in THF) was added. The mixture was allowed to stand at $0°$ C. for 16 hours and was then quenched with methanol. The mixture was diluted with ether and then washed sequentially with citric acid (aq) and brine. Drying $MgSO_4$) and evaporating provided an oil which was purified by silica gel chromatography to give the desired compound in 40% yield.

EXAMPLE 51

2(S)-t-Butyloxycarbonylamino-1-cyclohexyl-3(R),4(S)-dihydroxyhex-5-ene

An allylic oxidation using stoichiometric $SeO_2$ and t-butyl hydroperoxide (Umbriet, M. A. and Sharpless, K. B. *J. Am. Chem. Soc.* 1977, 99, 5526) was performed on the resultant product of Example 50 to give the desired product after silica gel chromatography.

EXAMPLE 52

Ethoxycarbonyl-Phe-Leu Amide of 2(S)-Amino-1-cyclohexyl-3(R),4(S)-dihydroxy-hex-5-ene Following the procedure of Example 15, but replacing the resultant product of Example 14 and Boc-Phe-His with the resultant product of Example 51 and ethoxycarbonyl-Phe-Leu, gave the desired product. Anal. calcd. for $C_{30}H_{47}N_3O_6$: C, 66.03 H, 8.68; N, 7.70. Found: C, 66.10; H, 8.83; N, 7.43.

EXAMPLE 53

(N-Butyl, 4-OCH₃)-Phenylalanine

To a stirred 0° C. suspension of (4-OCH₃)-phenylalanine (1.00 g, 5.12 mmol) and butyraldehyde (0.406 g, 110 M %) in methanol (10 mL) was added sodium cyanoborohydride (241 mg, 75 M %). The mixture was warmed to room temperature for 23 h and filtered. The solid was washed with methanol and suction dried to give 1.07 g (83%) of the desired product. Mass spectrum: $M^+ = 251$. Anal. Calcd for $C_{14}H_{21}NO_3 \cdot \frac{1}{2}H_2O$: C, 65.3; H, 8.5; N, 5.4 Found: C, 65.1; H, 8.3; N, 5.6.

EXAMPLE 54.

(N-Butyl, 4-OCH₃)Phe-His Amide of 2(S)-Amino-1-cyclohexyl-3(R),4(S)-dihydroxy-6-methylheptane Using the procedure of Example 21, but replacing TBA-CHA with the resultant product of Example 53 gave the desired compound. Mass spectrum: $(M+H)^+ = 614$.

Anal. Calcd for $C_{34}H_{55}N_5O_5 \cdot \frac{1}{2}H_2O$: C, 65.6; H, 9.1; N, 11.2. Found: C, 65.3; H, 9.0; N, 11.3.

EXAMPLE 55

H-(4-OCH₃)Phe-Leu Amide of 2(S)-Amino-1-cyclohexyl-3(R),4(S)-dihydroxy-6-methylheptane.

Using the procedure of Example 33, but replacing Boc-Phe-Ala with Cbz-(3-I,4-OCH₃)Phe-Leu provided the protected iodinated product. Deprotection and deiodination was achieved by hydrogenating 0.59 g in methanol (150 with NaOAc.3H₂O (0.40 g), 2.5% Rh/BaSO₄ (1.5 g), 20% Pd/C (0.29 g) at 4 atmospheres H₂ for 2.5 h. Filtration and evaporation provided a residue which was partitioned between ethyl acetate and sat. aq. NaHCO₃. The organic layer was washed with dilute Na₂S₂O₃ and brine, dried, filtered, and evaporated to give a solid. Recrystallization from CH₂Cl₂/hexane provided 260 mg (65%) of the desired compound. HRMS: M+Calcd for $C_{30}H_{52}N_3O_5$: 534.3907. Measured: 534.3925.

EXAMPLE 56

(N,N-Dimethyl,4-methoxy)-Phe-Leu Amide of 2(S)-Amino-1-cyclohexyl-3(R),4(S)-dihydroxy-6-methylheptane.

The resultant product of Example 55 (130 mg, 0.243 mmol) was hydrogenated (1 atmosphere H₂) with 10% Pd/C (39 mg) in methanol/formalin (12 mL/5 mL) for 8 h. Filtering and evaporating (high vacuum) provided a 0esidue which was chromatographed on silica gel to give 43 mg (32%) of the desired compound. HRMS: $(M+H)^+$ calculated for $C_{32}H_{56}N_3O_5$: 562.4220. Measured: 562:4230.

EXAMPLE 57

H-Phe-Leu Amide of 2(S)-Amino-1-cyclohexyl-3(R),4(S)-dihydroxy-6-methylheptane.

Following the procedure of Example 55, but replacing Cbz-(3-I,4-OCH₃)Phe-Leu with Cbz-Phe-Leu and omitting NaOAc.3H₂O and 2.5% Rh/BaSO₄ in the reduction step, provided the desired compound. Mass spectrum: $(M+H)^+ = 504$. Anal. Calcd for $C_{29}H_{49}N_3O_4$: C, 69.1; H, 9.8; N, 8.3. Found: C, 69.0; H, 10.1; N, 8 3.

EXAMPLE 58

[N-(2-Cyanoethyl)]Phe-Leu Amide of 2(S)-Amino-1-cyclohexyl-3(R),4(S)-dihydroxy-6-methylheptane.

A suspension of the resultant compound of Example 57 (297 mg, 0.590 mmol) in acrylonitrile (2 mL) was refluxed for 3 days. Evaporation provided a residue which was dissolved in ethyl acetate, filtered, evaporated and chromatographed on silica (dichloromethane/methanol, 97.5/2.5) to give 162 mg (49%) of the desired compound. Mass spectrum: $(M+H)^+ = 557$.

Anal Calcd for $C_{32}N_{52}N_4O_4$: C, 69.0; H, 9.4; N, 10.1. Found: C, 68.6; H, 9.5; N, 9.9.

EXAMPLE 59

[N-(3-Aminopropyl)]Phe-Leu Amide of 2(S)-Amino-1-cyclohexyl-3(R),4(S)-dihydroxy-6-methylheptane.

The resultant compound of Example 58 (75 mg, 0.135 mmol) was hydrogenated (4 atmospheres H₂) over Raney Nickel (85 mg) in anhydrous methanol/ammonia (20 mL/5 mL) for 3 h. Filtration and evaporation provided the desired product (68 mg). Mass spectrum: $(M+H)^+ = 561$.

EXAMPLE 60

(N,N-dimethyl)Gly-Phe-His Amide of 2(S)-Amino1-cyclohexy 1-3(R),4(S)-dihydroxy-6-methylheptane.

Using the procedure of Example 56, but replacing the resultant product of Example 55 with the resultant product of Example 64, gave the desired product. Mass spectrum: $(M+H)^+ = 613$.

EXAMPLE 61

Cbz-β-Ala-Phe-His Amide of 2(S)-Amino-1-cyclohexyl-3(R),4(S)-dihydroxy-6-methylheptane.

Using the procedure of Example 21, but replacing TBA-CHA with Cbz-B-Ala-Phe gave the desired compound. Mass spectrum: $(M+H)^+ = 733$. Analysis calculated for $C_{40}H_{56}N_6O_7$: C, 65.5; H, 11.5. Found: C, 65.2; H, 7.7; N, 11.2.

EXAMPLE 62

H-β-Ala-Phe-His Amide of 2(S)-Amino-1-cyclohexyl-3(R),4(S)-dihydroxy-6-methylheptane Diacetic Acid Salt.

The resultant compound of Example 61 (1.00 g, 1.36 mmol) in acetic acid (14 mL) was hydrogenated at 1 atmosphere with 10% Pd/C (0.50 g) for 3 h. Filtration, extraction of the catalyst with acetic acid, and evaporation of the combined acetic acid solutions gave a residue which was dissolved in water (25 mL) and lyophilized to provide 891 mg (91%) of the desired product. Mass spectrum: $(M+H)^+ = 559$ (free base). Analysis Calculated for $C_{36}H_{58}N_6O_9 \cdot \frac{1}{2}H_2O$: C, 59.4; H, 8.1; N, 11.5. Found: C, 59.3.; H, 8.0; N, 11.2.

EXAMPLE 63

Cbz-Sar-Phe-His Amide of 2(S)-Amino-1-cyclohexyl-3(R),4(S)-dihydroxy-6-methylheptane.

Using the procedure of Example 21, but replacing TBA-CHA with Cbz-Sar-Phe gave the desired compound. Mass spectrum: $(M+H)^+ = 733$. Anal. Calcd for C, 64.8; H, 7.7; N, 11 3. Found: 65.0; H, 7.6; N, 11.3.

EXAMPLE 64

H-Sar-Phe-His Amide of 2(S)-Amino-1-cyclohexyl-3(R),4(S)-dihydroxy-6-methylheptane Diacetic Acid Salt.

Using the procedure of Example 62, but replacing the resultant compound of Example 61 with the resultant compound of Example 63 gave the desired product. Mass spectrum: $(M+H)^+ = 599$ (free base). Anal. calcd for $C_{36}H_{58}N_6O_9 \cdot H_2O$: C, 58.7; H, 8.2; N, 11.4. Found: 58.5; H, 8.1; N, 11.4.

EXAMPLE 65

Cbz-GABA-Phe-His Amide of 2(S)-Amino-1-cyclohexyl-3(R),4(S)-dihydroxy-6-methylheptane.

Using the procedure of Example 21, but relacing TBA-CHA with Cbz-GABA-Phe (GABA is 4-aminobutyric acid) gave the desired compound.

EXAMPLE 66

H-GABA-Phe-His Amide of 2(S)-Amino1-cyclohexyl-3(R),4(S)-dihydroxy-6-methyl-heptane Diacetic Acid Salt.

Using the procedure of Example 62, but replacing the resultant compound of Example 61 with the resultant compound of Example 65 gave the desired product.

EXAMPLE 67

Cbz-Isonipectoyl-Phe-His Amide of 2(S)-Amino-1-cyclohexyl-3(R),4(S)-dihydroxy-6-methylheptane.

Using the procedure of Example 21, but replacing TBA-CHA with Cbz-Isonipectoyl-Phe gave the desired compound. Mass spectrum: $(M+H)^+ = 773$. Analysis calculated for $C_{43}H_{60}N_6O_7 \cdot H_2O$: C, 65.3; H, 7.9; N, 10.6. Found: 65.4; H, 7.6; H, 10.5.

EXAMPLE 68

H-Isonioectoyl-Phe-His Amide of 2(S)-Amino-1-cyclohexyl-3(R),4(S)-dihydroxy-6-methylheptane Diacetic Acid Salt.

Using the procedure of Example 62, but replacing the resultant compound of Example 61 with the resultant compound of Example 67 gave the desired product. Mass spectrum: $(M+H)^+ = 639$ (free base).

EXAMPLE 69

Cbz-D-Ala-Phe-His Amide of 2(S)-Amino-1-cyclohexyl-3(R),4(S)-dihydroxy-6-methylheptane.

Using the procedure of. Example 21, but replacing TBA-CHA with Cbz-D-Ala-Phe gave the desired compound. Mass spectrum: $(M+H)^+ = 733$. Analysis calculated for $C_{40}H_{56}N_6O_7 \cdot 1.5H_2O$: C, 63.2; H, 7.8; N, 11.0. Found: C, 63.0; H, 7.4; N, 11 0.

EXAMPLE 70

H-D-Ala-Phe-His Amide of 2(S)-Amino-1-cyclohexyl-3(R),4(S)-dihydroxy-6-methylheptane Diacetic Acid Salt.

Using the procedure of Example 62, but replacing the resultant compound of Example 61 with the resultant compound of Example 69 gave the desired product. Mass spectrum: $(M+H)^+ = 599$ (free base).

EXAMPLE 71

3-Benzyloxycarbonylamino-3-methylbutanoic Acid.

A solution of 2,2-dimethyl-3-carbomethyoxypropionic acid [LeMaul, Bull. Soc. Chim. Fr., 828 (1965), 20 g, 0.125 mol], diphenylphosphorylazide (34.3 0.125 mol) and triethylamine was heated in toluene (150 mL) at 100° C. for 2 h. After cooling to 5° C., the toluene solution was washed successively with 0.5M HCl, aqueous $NaHCO_3$ and brine. Evaporation of the dried solution gave a residue which was chromatographed on silica gel eluting with 60/40 hexane ether. There was obtained 13 g of methyl 3-isocyanato-3-methylbutanoate as a mobile liquid. A solution of this material in toluene (20 mL) was treated with benzyl alcohol (13 mL) and the resulting mixture heated at reflux for 40 h. Evaporation of the toluene left a residue which was dissolved in methanol (125 mL) and then treated with a solution of NaOH (6.6 g, 0.165 mol) in 22 mL of water. After 5 h, the reaction mixture was partially evaporated, washed with ether and acidified with 6N HCl. Extraction with methylene chloride and evaporation gave 21 g of the desired product. NMR (300 MHz, $CDCl_3$) 1.42 (s, 6H), 2.78 (s, 2H), 5.08 (s, 2H).

EXAMPLE 72

Cbz-[($\beta,\beta$-di-Me)-$\beta$-Ala]-Phe-OCH$_3$.

A 4.0 g sample of 3-benzyloxycarbonylamino-3-methylbutanoic acid was coupled to phenylalanine methyl ester hydrochloride (3.43 g) using the mixed anhydride procedure described in Example 2. Purification of the crude product by flash chromatography eluting with 65/35 ether-hexane gave an 86% yield of product. NMR (300 MHz, $CDCl_3$): 1.32 (s, 3H), 1.34 (s, 3H), 2.46 (d, 1H), 2.63 (d, 1H), 2.98 (dd, 1H), 3.09 (dd, 1H), 3.70 (s, 3H), 4.86 (dd, 1H), 4.97 (d, 1H), 5.2 (d, 1H), 5.3 (s, 1H), 6.13 (d, 1H).

EXAMPLE 73

Cbz-[($\beta,\beta$-di Me)-$\beta$-Ala]-Phe-OH

To a 0° C. solution of Cbz-[($\beta,\beta$-di-Me)-$\beta$-Ala]-Phe-OMe (1.5 g, 3.63 mmol) in dioxane (15 mL) was added a solution of lithium hydroxide (0.174 g, 4.15 mmol) in water (7.5 mL). After stirring for 1 h at 0°-5° C., the reaction mixture was diluted with cold water and extracted 2X with ether. The aqueous portion was acidified with 6N HCl and extracted with ether. The organic extract was washed with brine and evaporated to give an 87% yield of product as a viscous liquid.

EXAMPLE 74

Cbz-[(β,β-di-Me)-β-Ala]-Phe-His Amide of 2(S)-Amino-1-cyclohexyl-3(R),4(S)-dihydroxy-6-methylheptane.

Using the procedure of Example 21, but replacing TBA-CHA with Cbz-[(β,β-di Me)-β-Ala]-Phe gave the desired compound. Mass spectrum: $(M+H)^+ = 761$. Anal. Calcd for $C_{42}H_{60}N_6O_7 \cdot \frac{1}{2}H_2O$: C, 65.5; H, 8.0; N, 10.9. Found: C, 65.6; H, 7.9; N, 11.0.

EXAMPLE 75

H-[(β,β-di-Me)-β-Ala]-Phe-His Amide of 2(S)-Amino-1-cyclohexyl-3(R),4(S)-dihydroxy-6-methylheptane Diacetic Acid Salt.

Using the procedure of Example 62, but replacing the resultant compound of Example 61 with the resultant compound of Example 74 gave the desired product. Mass spectrum: $(M+H)^+ = 627$ (free base). Anal. Calcd for $C_{38}H_{62}N_6O_9 \cdot H_2O$: C, 59.7; H, 8.4; N, 11.0. Found: C, 59.5; H, 8.4; N, 11.3.

EXAMPLE 76

Cbz-Pro-Phe-His Amide of 2(S)-Amino-1-cyclohexyl-3(R),4(S)-dihydroxy-6-methyl-heptane.

Using the procedure of Example 21, but replacing TBA-CHA with Cbz-Pro-Phe gave the desired compound. Mass spectrum: $(M+H)^+ = 759$. Analysis calculated for $C_{42}H_{58}N_6O_7 \cdot \frac{1}{2}H_2O$: C, 65.7, H, 7.7; N, 10.9. Found: 65.7, H, 7.7; N, 10.9.

EXAMPLE 77

H-Pro-Phe-His Amide of 2(S)-Amino-1-cyclohexyl-3(R),4(S)-dihydroxy-6-methylheptane Acetic Acid Salt.

Using the procedure of Example 62, but replacing the resultant compound of Example 61 with the resultant compound of Example 76 gave the diacetic acid salt as a tacky solid. A portion of the di salt was partioned betwen satd. NaHCO3 and dichloromethane. The aqueous layer was further extracted with dichloromethane and the combined organic layers were dried, filtered and evaporated to give the desired product. Mass spectrum: $(M+H)^+ = 625$ (free base). Analysis calculated for $C_{36}H_{56}N_6O_7 \cdot 2H_2O$: C, 60.0; H, 8.4; N, 11.6. Found: C, 59.9; H, 7.9; N, 11.5.

EXAMPLE 78

3-Benzyloxycarbonylamino-2,2-dimethylpropionic Acid.

3-Carbomethoxy-3-methylbutanoic acid [Bull. Soc. Chim. Fr., 828 (1965), 7.85 g, 0.049 mol] was reacted with diphenylphosphorylazide and triethylamine as described in Example 71. After heating the toluene solution for 1.5 h, benzyl alcohol (8 g) was added directly to the reaction mixture and heating at reflux was continued for 20 h. Work-up and purification as in Example 71 gave methyl 3-benzyloxycarbonylamino-2,2-dimethylpropionate. NMR (300 MHz, CDCl3): 1.2 (s, 6H), 3.3 (d, 2H), 3.68 (s, 3H), 5.1 (s, 2H), 5.22 (m, 1H). A sample of the methyl ester (6.21 g, 0.023 mol) was saponified with 3.1 g (0.78 mol) of NaOH in 100 mL ethanol/10 mL H2O at room temperature for 48 h. Work-up as in Example 71 gave the desired product as a liquid. NMR (300 MHz, CDCl3): 1.23 (s, 6H), 3.32 (d, 2H), 5.10 (s, 2H), 5.27 (m, 1H).

EXAMPLE 79

Cbz-[(α,α-di-Me)-β-Ala]-Phe-OCH3.

To a solution of 3-benzyloxycarbonylamino-2,2-dimethylpropionic acid (1.5 g, 5.97 mmol) in methylene chloride (13 mL) was added oxalyl chloride (0.757 g, 5.97 mmol) and dimethylformamide (30 ul). After stirring for 1 h at room temperature, the reaction mixture was cooled to 0° C. and treated successively with phenylalanine methyl ester hydrochloride (1.29 g, 5.97 mmol) and N-methylmorpholine (1.81 g, 17.9 mmol). Stirring for 1 h at 0°-5° C. was followed by distribution between CH2Cl2 and 0.5N HCl. The organic phase was washed with aqueous NaHCO3 and brine and dried over MgSO4. Evaporation of the solvent gave a residue which was purified by chromatography. There was obtained a 69% yield of product as a liquid. NMR (300 MHz, CDCl3): 1.11 (s, 3H), 1.12 (s, 3H), 3.05 (dd, 1H), 3.18 (dd, 1H). 3.23 (d, 1H), 3.24 (d, 1H), 3.75 (s, 3H), 4.82 (dd, 1H), 5.08 (s, 2H), 5.37 (broad t, 1H), 6.04 (d, 1H).

EXAMPLE 80

Cbz-[(α,α-di-Me)-β-Ala]-Phe-OH.

The hydrolysis of the methyl ester was carried out by the procedure described in Example 71 to give the desired product in 90% yield as a viscous liquid.

EXAMPLE 81

Cbz-[α,α-di-Me)-β-Ala]-Phe-His Amide of 2(S)-Amino-1-cyclohexyl-3(R),4(S)-dihydroxy-6-methylheptane.

Using the procedure of Example 21, but replacing TBA-CHA with Cbz-[α,α-di-Me)-β-Ala]-Phe gave the desired compound. Mass spectrum: $(M+H)^+ = 761$.

EXAMPLE 82

[(α,α-Di-Me)-β-Ala]-Phe-His Amide of 2(S)-Amino-1-cyclohexyl-3(R),4(S)-dihydroxy-6-methylheptane Bis acetic acid salt.

Using the compound from Example 81 and the procedure of Example 62 gave the desired product in 71% yield. Mass spectrum: $(M+H)^+ = 627$.

EXAMPLE 83

Cbz-Phe-His Amide of 2(S)-Amino-1-cyclohexyl-3(R),4(S)-dihydroxy-6-methylheptane Using the procedure of Example 21 but replacing TBA-CHA with Cbz-Phe gave the desired compound. Mass spectrum: $(M+H)^+ = 661$.

EXAMPLE 84

Phe-His Amide of 2(S)-Amino-1-cyclohexyl-3(R),4(S)-dihydroxy-6-methylheptane.

A solution of the product from Example 83 (180 mg, 0.273 mmol) in methanol (50 mL) was hydrogenolyzed in a Parr Apparatus with 90 mg of 20% Pd/C and 4 atmospheres of hydrogen. After the hydrogen uptake ceased, the catalyst was filtered and the filtrate evaporated to the desired product (90 mg, 63%). Mass spectrum: $(M+H)^+ = 527$.

EXAMPLE 85

α-Aminoisobutyryl-Phe-His Amide of 2(S)-Amino-1-cyclohexyl-3(R),4(S)-dihydroxy-6-methylheptane.

A mixture of a α-aminoisobutyric acid N-carboxy anhydride (10.9 mg, 0.085 mmol) and the product from Example 84 (44.6 mg, 0.085 mmol) in dimethylformamide (3 mL) was stirred at room temperature for 16 h. The dimethylformamide was evaporated in vacuo and the residue was distributed between chloroform and water. The organic phase was dried and evaporated to a residue which was chromatographed on silica gel eluting with methanol-chloroform mixtures. There was obtained 35 mg (68%) of the desired product. Mass spectrum: $(M+H)^+ = 612$.

EXAMPLE 86

(Pyridin-3-yl-sulfonyl)-Phe-His Amide of 2(S)-Amino-1-cyclohexyl-3(R),4(S)-dihydroxy-6-methylheptane.

Using the procedure of Example 21, but replacing TBA-CHA with (pyridin-3-yl-sulfonyl)-Phe gave the desired product.

EXAMPLE 87

(Pyrazin-2-yl-carbonyl)-Phe-His Amide of 2(S)-Amino-1-cyclohexyl-3(R),4(S)-dihydroxy-6-methylheptane.

Using the procedure of Example 21, but replacing TBA-CHA with (pyrazin-2-yl-carbonyl)-Phe gave the desired product. Mass spectrum: $(M+H)^+ = 634$. Anal. Calcd for $C_{34}H_{47}N_7O_5 \cdot \frac{1}{4}H_2O$: C,64.0; H, 7.5; N, 15.4. Found: C, 63.9; H, 7.6; N. 15.2.

EXAMPLE 88

(Imidazol-4-yl-acetyl)-Phe-Leu Amide of 2(S)-Amino-1-cyclohexyl-3(R),4(S)-dihydroxy-6-methylheptane.

Using the coupling conditions of Example 21 with 4-imidazoleacetic acid and the resultant product of Example 57 provided the desired product. Mass spectrum: $(M+H)^+ = 612$. Analysis calculated for $C_{34}H_{53}N_5O_5 \cdot \frac{1}{2}H_2O$: C, 65.9; H, 8.9; N, 11.3. Found: C, 65.9; H, 8.9; N, 11.3

EXAMPLE 89

(Pyrrol-2yl-carbonyl)-Phe-His Amide of 2(S)-Amino-1-cyclohexyl-3(R),4(S)-dihydroxy-6-methylheptane.

Using the procedure of Example 21, but replacing TBA-CHA with (pyrrol-2-yl-carbonyl)-Phe gave the desired product. Mass spectrum: $(M+H)^+ = 621$.

EXAMPLE 90

Allyloxycarbonyl-Phe-Leu Amide of 2(S)-Amino-1-cyclohexyl-3(R),4(S)-dihydroxy-6-methylheptaine.

Using the procedure of Example 33, but replacing Boc-Phe-Ala with allyloxy carbonyl Phe-Leu provided the desired product. Mass spectrum: $(M+H)^+ = 588$. Anal. Calcd for $C_{33}H_{53}N_3O_6$: C, 67.4; H, 9.1; N, 7.2. Found: C, 67.6; H, 9.0; N, 7.1.

EXAMPLE 91

3-Hydroxypropyloxycarbonyl-Phe-Leu Amide of 2(S)-Amino-1-cyclohexyl-3(R),4(S)-dihydroxy-6-methylheptane.

To a stirred 0° solution of the resultant compound of Example 90 (1.25 g, 2.13 mmol) in dry tetrahydrofuran (THF, 50 mL) was added 9-borabicyclo[3.3.1]- nonane (9-BBN, 25.5 mL of a 0.5M solution in THF). The mixture was warmed to room temperature for 12 h and then cooled to 0° C. Water (15 mL) and 3M NaOH (4.5 mL) were added followed 2 min later by 30% $H_2O_2$ (5 mL). The mixture was partitioned between brine (20 mL) and ethyl acetate (100 mL). The organic phase was washed (brine), dried ($Na_2SO_4$), filtered, and evaporated to a thick oil. Recrystallization twice (dichloromethane/ether) provided 670 mg (52%) of the desired compound. Mass spectrum: $(M+H)^+ = 605$. Analysis calculated for $CC_{33}H_{55}N_3O_7$: C, 65.4; H, 9.2; N, 6.9. Found: C, 65.4; H, 9.1; N, 6.8.

EXAMPLE 92

Cbz-Gly Ester of the Resultant Compound of Example 91 (at 3-Hydroxypropyloxy Group).

To a stirred 0° C. suspension of the resultant compound of Example 91 (60 mg, 0.099 mol), Cbz-Gly-OH (20.7 mg, 0.099 mmol), and 4-dichloromethane (10 mL) was added ethyldimethylaminopropyl carbodiimide hydrochloride (38 mg, 0.198 mmol). The mixture was warmed at room temperature for 15 h and then diluted with dichloromethane and washed sequentially with 1M $H_3PO_4$, satd $NaHCO_{33}$ and brine. Drying ($Na_2SO_4$), filtering, and evaporating provided 57 mg (72%) of the desired compound. Mass spectrum: $(M+H)^+ = 797$.

EXAMPLE 93

H-Gly-Ester of the Resultant Compound of Example 91 (at 3-Hydroxypropyloxy Group).

The resultant compound of Example 92 (13 mg, 0.016 mmol) was hydrogenated (1 atmosphere $H_2$) with 10% Pd/C (4 mg) in methanol for 3 h. Filtration, evaporation and chromatography on silica (dichloromethane/methanol, 95/5- 90/10) provided 4 mg (37%) of the desired product. HRMS: $(M+H)^+$ calcd for $C_{35}H_{58}N_4O_8$: 663.4333. Found: 663.4355.

EXAMPLE 94

Lysine Ester of the Resultant Compound of Example 91 (at 3-Hydroxypropyloxy Group) Diacetic Acid Salt.

Following the procedure of Example 92 but replacing Cbz-Gly-OH with a,e-di- Cbz-Lys-OH provide the desired protected peptide. Hydrogenation according to the procedure of Example 93, but replacing methanol with acetic acid provide the desired compound.

EXAMPLE 95

Hemisuccinate Ester of the Resultant Compound of Example 91 (at 3-Hydroxypropyloxy Group).

Using the procedure of Example 92, but replacing Cbz-Gly with benzyl succinate provided the protected product. Deprotection was achieved by following the procedure of Example 103 to give the desired product.

EXAMPLE 96

Phosphate Ester of the Resultant Compound of Example 91 (at 3-Hydroxypropyloxy Group).

Using the procedure of Example 92, but replacing Cbz-Gly with dibenzylphosphate provided the protected product. Deprotection was achieved by following the procedure of Example 103 to give the desired product.

EXAMPLE 97

2(R,S),3-Dihydroxypropyloxycarbonyl-Phe-Leu Amide of 2(S)-Amino-1-cyclohexyl-3(R),4(S)-dihydroxy-6-methylheptane.

Following the procedure of Example 14, but replacing the resultant compound of Example 13 with the resultant compound of Example 90, and heating the mixture at 50° C. for 24 h, gave the desired product. Mass spectrum: $(M+H)^+ = 622$. Anal. Calcd for $C_{33}H_{55}N_3O_8 \cdot \frac{1}{2}H_2O$: C, 62.8; H, 8.9; N, 6.7. Found: C, 63.0; H, 8.6; N, 6.7.

EXAMPLE 98

Cbz-Gly Mono- and Diesters of the Resultant Compound of Example 97 (at the 3-Hydroxypropyloxy and 2,3-Dihydroxypropyl Groups, Respectively).

Using the procedure of Example 92, but replacing the resultant compound of Example 91 with the resultant compound of Example 97, provided a mixture of the desired mono- and diesters. Separation was achieved by silica gel chromatography.

EXAMPLE 99

H-Gly-Ester of the Resultant Compound of Example 97 (at the 3-Hydroxypropyl Group) Acetic Acid Sat.

Using the procedure of Example 93, but replacing the resultant compound of Example 92 with the resultant monoester of Example 98 and replacing methanol with acetic acid, gave the desired product.

EXAMPLE 100

H-Gly-Diester of the Resultant Compound of Example 97 (at the 2,3-Dihydroxypropyl Group) Diacetic Acid Salt.

Using the procedure of Example 93, but replacing the resultant compound of Example 92 with the resultant diester of Example 98 and replacing methanol with acetic acid, provided the desired compound.

EXAMPLE 101

Ethoxycarbonyl-(OBn)Thr-His Amide of 2(S)-Amino-1-cyclohexyl-3(R),4(S)-dihydroxy-6-methylhexane.

Using the procedure of Example 21, but replacing TBA-CHA with ethoxycarbony-threonine benzyl ether [(OBn)Thr] gave the desired compound. Mass spectrum: $(M+H)^+ = 616$. Calcd for $C_{32}H_{49}N_5O_7$: C, 62.4; H, 8.0; N, 11.4. Found: 62.3; H, 8.0; N, 11.3.

EXAMPLE 102

Benzyloxyacetyl-Phe-His Amide of 2(S)-Amino-1-cyclohexyl-3(R),4(S)-dihydroxy-6-methylheptane.

Using the procedure of Example 21, but replacing TBA-CHA with benzyloxyacetyl-Phe gave the desired compound. Mass spectrum: $(M+H)^+ = 676$. Analysis calculated for $C_{38}H_{53}N_5O_6 \cdot \frac{1}{4}H_2O$: C, 67.1; H, 7.9; N, 10.3. Found: 67.0; H, 7.9; N, 10.2.

EXAMPLE 103

Hydroxyacetyl-Phe-His Amide of 2(S)-Amino-1-cyclohexyl-3(R),4(S)-dihydroxy-6-methylheptane.

The resultant compound of Example 102 (250 mg, 0.370 mmol) in acetic acid (3.7 mL) was hydrogenated at 1 atmosphere $H_2$ with 10% Pd/C (125 mg) for 23 h. Filtration, extraction of the catalyst with acetic acid, and evaporation of the combined acetic acid solutions gave a residue which was partitioned between ethyl acetate and satd. aq. $NaHCO_3$. Exhaustive extraction of the aqueous phase with ethyl acetate, combination of all organic layers, and evaporation provided crude product which was recrystallized (ethylacetate/methanol/methylcyclohexane) to give 157 mg (72%) of the desired product. Mass spectrum: $(M+H)^+ = 586$. Anal. Calcd for $C_3H_{47}N_5O_6 \cdot H_2O$: C, 61.7; H, 8.2; N, 11.6. Found: C, 62.1; H, 8.1; N, 11.4.

EXAMPLE 104

Acetyl-$\beta$-Ala-Phe-His Amide of 2(S)-Amino-1-cyclohexyl-3(R),4(S)-dihydroxy-6-methylheptane.

Using the procedure of Example 21, but replacing TBA-CHA with Acetyl-$\beta$-Ala Phe provided the entire compound.

EXAMPLE 105 i-Bu-Pl-His Amide of 2(S)-Amino-1-cyclohexyl-3(R),4(S)-dihydroxy-6-methylheptane.

Using the procedure of Example 21, but replacing TBA-CHA with O-isobutyl-L-3-phenyllactic acid (i-Bu-Pl-OH) gave the desired compound.

EXAMPLE 106

Isobutyryl-Homo-Phe methyl ester

To a suspension of (+)-$\alpha$-amino-4-phenylbutyric acid (Homo Phe) methyl ester hydrochloride (0.83 g, 3.61 mmol) in methylene chloride cooled in an ice bath was added successively isobutyric anhydride (0.57 g, 3.61 mol) and N-methylmorpholine (0.79 mL, 7.22 mmol). After stirring for 30 min at 0°–5° C., the reaction mixture was distributed between methylene chloride and 0.5N HCl. The organic layer was washed with aqueous $NaHCO_3$ and brine solution and then dried over $MgSO_4$. Evaporation of the solvent gave a solid residue which was triturated with hexane to provide 700 mg of product, mp 72°–73°.

EXAMPLE 107

Isobutyryl-Homo-Phe

The hydrolysis of the methyl ester was carried out by the procedure described in Example 73 to give the desired product in 90% yield.

EXAMPLE 108

Isobutyryl-Homo-Phe-His Amide of 2(S)-Amino-1-cyclohexyl-3(R),4(S)-dihydroxy-6-methylheptane.

Using the procedure of Example 21, but replacing TBA-CHA with isobutyryl-homo- Phe gave the desired compound. Mass spectrum: (M+H)+ =612.

EXAMPLE 109

2(S)-[[(4-Morpholinyl)carbonyl]oxy]-3-phenylpropionic acid methyl ester.

To L-phenyllactic acid methyl ester (3.2 g) was added 150 mL of 12.5% phosgene in toluene and 25 drops of dimethylformamide. After stirring for 16 h at room temperature, the solvent was evaporated and the residue chased several times with benzene. The resulting product was dissolved in methylene chloride (50 mL), cooled to 0° C. and treated by dropwise addition with 3.86 g (0.044 mol) of morpholine. The reaction mixture was stirred for 2 h at 0°-5° C. and then distributed between 0.5N HCl and methylene chloride. The organic phase was washed with aqueous NaHCO$_3$ and brine and evaporated to a residue. Flash chromatography on silica gel eluting with 2/1 ether hexane gave a 65% yield of product. NMR (300 MHz): 3.08 (dd, 1H), 3.20 (dd, 1H), 3.8 (s, 3H), 5.19 (dd, 1H).

EXAMPLE 110

2(S)-[(4-Morpholinyl)carbonyl]oxy-3-phenylpropionic acid.

Using the hydrolysis procedure of Example 73, the title compound was obtained in 90% yield.

EXAMPLE 111

2(S)-[(4-Morpholinyl)carbonyl]oxy-3-phenylpropionyl-His Amide of 2(S)-Amino-1-cyclohexyl-3(R),4(S)-dihydroxy-6-methylheptane.

Using the procedure of Example 21, put replacing TBA-CHA with the product from Example 110, gave the desired product in 60% -yield. Mass spectrum: (M+H)+ =642.

EXAMPLE 112

2(S)-[[(4-Cbz-1-Piperazinyl)carbonyl]oxy]-3-phenylpropionic acid methyl ester

Using the procedure of Example 109, but replacing morpholine with Cbz- piperazine, gave the desired product in 63% yield.

EXAMPLE 113

2(S)-[[(4-Cbz-1-Piperazinyl)carbonyl]oxy])-3-phenylcrooionic acid.

Using the hydrolysis procedure of Example 73 gave the desired product in 93% yield.

EXAMPLE 114

2(S)-[[(4-Cbz-1-Piperazinyl)carbonyl]oxy]-3-phenylpropionyl-Phe-His Amide of 2(S)-Amino-1-cyclohexyl-3(R),4(S)-dihydroxy-6-methylheptane.

Using the procedure of Example 21, but replacing TBA-CHA with the resultant compound from Example 113, gave the title compound. Mass spectrum: (M+H)+ =775.

EXAMPLE 115

2(S)-[[(1-Piperazinyl)carbonyl]oxy]-3-phenylpropionyl-Phe-His Amide of 2(S)-Amino-1-cyclohexyl-3(R),4(S)-dihydroxy-6-methylheptane.

Using the procedure of Example 62 gave the title compound in 85% yield. M.p. 158°-160° C.

EXAMPLE 116

[(4-Morpholinyl)carbonyl]-Phe methyl ester.

A suspension of L phenylalanine methyl ester hydrochloride (6 g) in toluene (125 mL) was heated to 100° C. while phosgene gas was bubbled into the reaction mixture. After approximately 1-½-2 h, the mixture became homogeneous. The passage of phosgene was continued for an additional 15 min, keeping the temperature at 90°-100° C. The toluene was then evaporated and the residue chased several times with benzene. A 6.5 g (0.03167 mol) sample of a-isocyanato-L-phenylalanine methyl ester was dissolved in 50 mL of methylene chloride and cooled to 0° C. Morpholine (2.76 mL, 0.03167 mol) dissolved in 5 mL of methylene chloride was added dropwise. After 10 min at 0°-5° C., the reaction mixture was distributed between 0.5N HCl and methylene chloride. The organic layer was washed with aqueous NaHCO$_3$ and dried over MgSO$_4$. Evaporation of the solvent gave 7 g of product after trituration with hexane, mp 90°-91°.

EXAMPLE 117

[(4-Morpholinyl)carbonyl]-Phe.

Using the procedure of Example 73 gave the title compound in 89% yield.

EXAMPLE 118

[(4-Morpholinyl)carbonyl]-Phe-His Amide of 2(S)-Amino-1-cyclohexyl-3(R),4(S)-dihydroxy-6-methylheptane.

Using the procedure of Example 21, but replacing TBA-CBA with [(4-morpholinyl)carbonyl]-Phe, gave the desired compound. Mass spectrum: (M+H)+ =642.

EXAMPLE 119

(Dimethylamino)carbonyl]-Phe-His Amide of 2(S)-Amino-1-cyclohexyl-3(R),4(S)-dihydroxy-6-methylheptane.

Using the procedures of Examples 116, 73, and 21, this compound was prepared. Mass spectrum: (M+H)+ =599.

EXAMPLE 120

[[Methyl-(2-hydroxyethyl)amino]carbonyl]-Phe-His Amide of 2(S)-Amino-1-cycloboxyl-3(R),4(S)-dihydroxy-6-methylheptane.

Using the procedures of Examples 116, 73, and 21, the title compound was synthesized. Anal. calcd for $C_{32}H_{52}N_6O_6 \cdot 1\frac{1}{2}$ H$_2$O: C, 60.44; H, 8.45; N, 12.82. Found: C, 60.36; H, 8.11; N, 12.77.

EXAMPLE 121

[(1-Cbz-4-Piperazinyl)carbonyl]-Phe methyl ester.

Using the procedure of Example 116, but replacing morpholine with 1-Cbz-piperazine, gave the desired product, mp 114°–115°.

EXAMPLE 122

[(1-Cbz-4-Piperazinyl)carbonyl]-Phe

Using the procedure of Example 73 gave the desired product in 89% yield.

EXAMPLE 123

[(1-Cbz-4-Piperazinyl)carbonyl]-Phe-His Amide of 2(S)-Amino-1-cyclohexyl-3(R),4(S)-dihydroxy-6-methylheptane.

Using the procedure of Example 21, but replacing TBA-CHA with [(1-Cbz-4-piperazinyl)carbonyl]-Phe, gave the desired compound.

EXAMPLE 124

[(1-Piperazinyl)carbonyl]-Phe-His Amide of 2(S)-Amino-1-cyclohexyl-3(R),4(S)-dihydroxy-6-methylheptane Bis-Acetic Acid Salt.

Using the procedure of Example 62 gave the desired compound in 90% yield. Mass spectrum: $(M+H)^+ = 640$ (free base).

EXAMPLE 125

[(4-Morpholinyl)carbonyl]-(4-OCH$_3$)Phe methyl ester.

Using the procedure of Example 116 but replacing H-Phe-OCH$_3$.HCl with L-tyrosine methyl ester methyl ether.HCl gave the title compound.

EXAMPLE 126

[(4-Morpholinyl)carbonyl]-(4-OCH$_3$)Phe-OH.

Using the procedure of Example 73 gave the title compound in 92% yield.

EXAMPLE 127

[(4-Morpholinyl)carbonyl]-(4-OCH$_3$)Phe-His Amide of 2(S)-Amino-1-cyclohexyl-3(R),4(S)-dihydroxy-6-methylheptane Using the procedure of Example 21, but replacing TBA-CHA with [(4-morpholinyl)carbonyl]-(4-OCH$_3$)Phe gave the desired compound. Mass spectrum: $(M+H)^+ = 671$.

EXAMPLE 128

[4-(2-Oxopiperazinyl)carbonyl]-Phe methyl ester.

Using the procedure of Example 116, but replacing morpholine with 2-oxopiperazine [Transition Met. Chem., 11, 27 (1986)] gave the desired compound in 80% yield.

EXAMPLE 129

[4-(2-Oxopiperazinyl)carbonyl]-Phe.

Using the procedure of Example 73 gave the desired compound.

EXAMPLE 130

[4-(2-Oxopiperazinyl)carbonyl]-Phe-His Amide of 2(S)-Amino-1-cyclohexyl-3(R),4(S)-dihydroxy-6-methylheptane.

Using the procedure of Example 21, but replacing TBA-CHA with (4-(2-oxopiperazinyl)carbonyl]-Phe, gave the desired product in 60% yield.

EXAMPLE 131

[1-(4-Oxopiperidinyl)carbonyl]-Phe methyl ester.

Using the procedure of Example 116, but replacing morpholine with 4-oxopiperidine gave the desired compound.

EXAMPLE 132

[1-(4-Oxopiperidinyl)carbonyl]-Phe.

Using the procedure of Example 73 gave the desired compund in 91% yield.

EXAMPLE 133

[1-(4-Oxopiperidinyl)carbonyl]-Phe-His Amide of 2(S)-Amino-1-cyclohexyl-3(R),4(S)-dihydroxy-6-methylheptane.

Using the procedure of Example 21, but replacing TBA-CHA with [1-(4-oxopiperidinyl)carbonyl]-Phe, gave the desired product.

EXAMPLE 134

[1-(4-Hydroxypiperidinyl)carbonyl]-Phe methyl ester.

Using the procedure of Example 116, but replacing morpholine with 4-hydroxypiperidine gave the desired compound.

EXAMPLE 135

[1-(4-Hydroxypiperidinyl)carbonyl]-Phe.

Using the procedure of Example 73, gave the desired product in 82% yield.

EXAMPLE 136

[1-(4-Hydroxypiperidinyl)carbonyl]-Phe-His Amide of 2(S)-Amino-1-cyclohexyl-3(R),4(S)-dihydroxy-6-methylheptane.

Using the procedure of Example 21, but replacing TBA-CHA with [1-(4-hydroxypiperidinyl)carbonyl]-Phe, gave the desired compound in 56% yield.

EXAMPLE 137

[1-(3-Hydroxypiperidinyl)carbonyl-Phe-His Amide of 2-(S)-Amino-1cyclohexyl-3(R),4(S)-dihydroxy-6-methylheptane.

Using the procedures described in Examples 116, 73 and 21, the title compound was synthesized.

EXAMPLE 138

3-Carbomethoxy-3-phenoxypropionic acid.

A solution of 2 phenoxybutyrolactone [Dareman, C., Bull. Soc. Chim. Fr., 294 (1971), 4.96 g, 0.028 mol] was added to methanol (125 mL) containing 0.054 mol of sodium methoxide. After stirring for 3.5 hours at room temperature, the mixture was quenched with 5 mL of acetic acid, and then distributed between ether and brine solution. The organic layer was washed with brine and evaporated to a residue (methyl-4-hydroxy-2- phenoxybutyrate). A solution of this material in acetone (300 mL) was treated with Jones solution until the orange color persisted. The acetone was partially evaporated and the residue was distributed between ether and brine solution. Evaporation of the dried ether layer gave the desired product as a waxy solid. NMR (300 NMR, CDCl$_3$): 3.02 (d, 2H), 3.78 (s, 3H), 5.11 (t, 1H).

EXAMPLE 139

3-[(4-Morpholinyl)carbonyl]-2phenoxypropionic acid methyl ester.

Using the mixed anhydride procedure described in Example 2, morpholine was coupled to 3-carbomethoxy-3-phenoxypropionic acid to give the desired product in 86% yield, mp 83°–84° C. Anal. Calcd for C$_{15}$H$_{19}$NO$_5$: C, 61.42; H, 6.53; N, 4.78. Found: C, 61.47; H, 6.50; N, 4.61.

EXAMPLE 140

3-[(4-Morpholinyl)carbonyl]-2-phenoxypropionic acid.

Using the procedure of Example 73 gave the desired product in 59% yield, mp 150°–151° C.

EXAMPLE 141

3-[(4-Morpholinyl)carbonyl]-2(R,S)-phenoxypropionyl-His Amide of 2(S)-Amino-1-cyclohexyl-3(R),4(S)-dihydroxy-6-methylheptane.

Using the procedure of Example 21, but replacing TBA-CHA with the resultant product of Example 140, gave the desired product as a mixture of R and S diastereomers. Chromatography on silica (dichloromethane/methanol, 95/5) provided the less polar diastereomer (isomer A) and the more polar diastereomer (isomer B). Isomer A: Mass spectrum: (M+H)$^+$ =642. Analysis calculated for C$_{34}$H$_{51}$N$_5$O$_7$.½H$_2$): C, 62.7; H, 8.0; N, 10.7. Found: C, 62.7; H, 8.1; N, 10.3. Isomer B: Mass spectrum: (M+H)$^+$ =642. Analysis calculated for C$_{34}$H$_{51}$N$_5$O$_7$.H$_2$O: C, 61.9; H, 8.1; 10.6. Found: C, 62.2; H, 7.8; N, 10.4.

EXAMPLE 142

2(R,S)-(4-Morpholinylcarbonylmethyl)-3-phenylpropionic Acid.

Ethyl a-carboxymethylcinnamate was prepared as reported (Cohen, S. G. and Milovanovic, A. *Biochemistry*, 1968, 3495) and hydrogenated according to the procedure of Example 93. The resulting dihydrocinnamate was coupled to morpholine using the procedure of Example 21. Ester hydrolysis according to the procedure of Example 73 provided the desired compound. Mass spectrum: (M+H)$^+$ =278. Anal. Calcd for C$_{15}$H$_{13}$NO$_4$.½H$_2$O: C, 64.4; H, 6.9; N, 5.0. Found: C, 64.4; H, 6.8; N, 4.9.

EXAMPLE 143

23(R,S)-(4-Morpholinylcarbonylmethyl)-3-phenylpropionyl-His Amide of 2(S)-Amino-1-cyclohexyl-3(R),4(S)-dihydroxy-6-methylheptane.

Using the procedure of Example 21, but replacing TBA-CHA with 2(R,S)-(4-morpholinylcarbonylmethyl)-3-phenylpropionic acid provided the desired product as a mixture of R and S diastereomers. Chromatography on silica (dichloro- methane/methanol 95/5–90/10) provided the less polar diastereomer (isomer A) and the more polar diastereomer (isomer B). Isomer A: Mass spectrum: (M+H)$^+$ =640. Anal. Calcd for C$_{35}$H$_{53}$N$_5$O$_6$.½H$_2$O: C, 64.8; H, 8.4; N, 10.8. Found: C, 65.1; H, 8.4, N, 10.3. Isomer B: Mass spectrum: (M+H)$^+$ =640. Anal. Calcd for C$_{35}$H$_{53}$N$_5$O.½H$_2$O: C, 64.8; H, 8.4; N, 10.8. Found: C, 65.0; H, 8.3; N, 10.6.

EXAMPLE 144

N-(Benzylosyacetyl)morpholine.

Using the mixed anhydride procedure described in Example 2, morpholine was coupled to benzyloxyacetic acid to give the desired product in 90% yield.

EXAMPLE 145

Methyl 2-benzyl-3-benzyloxy-3-[(4-morpholinyl)carbonyl]propionate.

A −78° C. solution of N-(benzyloxyacetyl)morpholine (1 g, 8.5 mmol) in THF (25 mL) was treated with potassium bis(trimethylsilyl)amide (17 mL of a 0.5M solution). After stirring for 10 min at −78° C., a solution of methyl 2-bromo-3-phenylpropionate (8.5 mmol) in THF (5 mL) was added dropwise. Stirring at −78° C. for 30 min was followed by warming to 0° C. The reaction was then distributed between ether and brine solution. The organic layer was washed with brine and dried over MgSO4. Evaporation and flash chromatography on silica gel gave the desired product in 63% yield.

EXAMPLE 146

2-Benzyl-3-hydroxy-3-[(4-morpholinyl)carbonyl]-propionic acid.

Using the procedure of Example 84, the benzyl ether protecting group was removed by catalytic hydrogenolysis to give methyl 2-benzyl-3-hydroxy-3-[(4- morpholinyl) carbonyl]propionate. The methyl ester function was hydrolyzed using the procedure in Example 73 to give the title compound.

EXAMPLE 147

2-Benzyl-3-hydroxy-3-[(4-morpholinyl)carbonyl]propionyl-His Amide of 2(S)-Amino-1-cyclohexyl-3(R),4(S)-dihydroxy-6-methylheptane.

Using the procedure of Example 21, but replacing TBA-CHA with 2-benzyl-3-hydroxy-3-[(4-morpholinyl)carbonyl]propionic acid, gave the desired product in 51% yield.

EXAMPLE 148

2-Hydroxy-3-[(4-morpholinyl]carbonyl]propionic acid acetonide.

A mixture of dl-malic acid (5 g), 2,2-dimethoxypropane (100 mL) and catalytic p TsOH was heated at 100° C. for 5 h. After cooling and evaporation the residual solid was recrystallized from carbon tetrachloride to give the corresponding acetonide lactone. This material was coupled to morpholine using the mixed anhydride procedure of Example 2 to give the title compound.

EXAMPLE 149

Methyl 2-hydroxy-3-[(4-morpholinyl)carbonyl]propionate.

A solution of 2-hydroxy-3-[(4-(morpholinyl)-carbonyl]propionic acid acetonide (5 g) in methyl alcohol (75 mL) was treated with 1 mL of concentrated sulphuric acid and the mixture was stirred for 24 h at room temperature. Partial evaporation of the solvent gave a residue which was distributed between either and brine solution. The ether layer was dried over $MgSO_4$ and evaporated to give the desired product.

EXAMPLE 150

Methyl 2-anilino-3-[(4-morpholinyl)carbonyl]propionate.

The trifluoromethanesulfonate of methyl 2-hydroxy-3-[4-morpholinyl)carbonyl] propionate was prepared by the method of Shiosaki [J. Org. Chem., 46, 3230 (1981)]. A solution of this compound (7 mmol) in methylene chloride (25 mL) was added dropwise within 5 minutes at room temperature to a stirred solution of aniline (14 mmol) in methylene chloride (25 mL), and stirring continued for 30 min at room temperature. The reaction mixture was filterd, the solution was washed with water, dried over $Na_2SO_4$, concentrated and the residue purified by chromatography. Yield of product = 80%.

EXAMPLE 151

2-Anilino-3-[(4-morpholinyl)carbonyl]propionyl-His Amide 2(S)-Amino-1-cyclohexyl-3(R),4(S)-dihydroxy-6-methylheptane.

Using the product from Example 150 and the methods of Examples 73 and 21 gave the title compound.

EXAMPLE 152

Ethyl 5-Acetamido-2(R,S)-benzyl-4-oxopentanoate.

Ethyl a-carboxymethylcinnamate was prepared as reported (Cohen, S. G. and Milovanovic, A. *Biochemistry*, 1968, 3495) and hydrogenated according to the procedure of Example 93. The resulting acid was converted to the desired acetamidomethyl ketone using the methodology of Pfaltz et al., (*Tetrahedron Lett.* 1984, 25, 2977: acid to acid chloride to cyanoketone followed by Zn/acetic acid/acetic anhydride treatment).

EXAMPLE 153

5-Acetamido-2(R,S)-benzyl-4-oxopentanoyl-His Amide of 2(S)-Amino-1-cyclohexyl-3(R),4(S)-dihydroxy-6-methylheptane.

The resultant product of Example 152 was hydrolyzed according to the procedure of Example 73 provided the corresponding acid which was coupled in place of TBA-CHA according to the procedure of Example 21. The desired product was obtained as an (R,S) mixture which was separated by chromatography.

EXAMPLE 154

3-[(4-Morpholinyl)carbonyl]-2-thiophenoxypropionic acid methyl ester.

Using the procedure of Example 139, but replacing 3-carbomethoxy-3-phenoxypropionic acid with 3-carbomethoxy-3-thiophenoxypropionic acid, gave the desired

EXAMPLE 155

3-[(4-Morpholinyl)carbonyl]-2-(R,S)-thiophenoxypropionyl-His Amide of 2(S)-Amino-1-cyclohexyl-3(R),4(S)-dihydroxy-6-methylheptane.

Using the procedures of Examples 73 and 21, the title compound was prepared in 49% overall yield.

EXAMPLE 156

2(S)-t-Butyloxycarbonylamino-1-cyclohexyl-3-hydroxy-6-methylheptan-4-one.

To a solution of resultant compound of Example 13 (8.50, 27.5 mmol) in dry THF (150 mL) were added $OsO_4$ (2.8 mL of a 2.5% solution in t-butanol and N-methylmorpholine N-oxide (9.28 g, 68.7 mmol). After 4d the mixture was partitioned between either (200 mL) and brine (100 mL). The aqueous layer was back extracted with either (2×100 mL), and the combined organic phase was washed with 10% $Na_2SO_3$, 0.1M $H_3PO_4$, and brine. Drying ($MgSO_4$) and evaporating provided a residue (10.81 g) which was chromatographed on silica gel to remove the four diastereomeric diols from 0.70 g (7%) of the desired product. Mass spectrum: $(M+H)=342$.

EXAMPLE 157

Boc-Phe-His Amide of 2(S)-t-Butyloxycarbonylamino-1-cyclohexyl-3-hydroxy-6-methylheptan-4-one.

The resultant product of Example 156 (220 mg, 0.645 mmol) was treated with 4M HCl/dioxane for 6 hours. Evaporation and drying under high vacuum provided the corresponding amine hydrochloride which was dissolved in dry dimethylformamide (DMF, 1.0 mL), treated with Boc-Phe-His (260 mg), N-methylmorpholine (0.142 mL), and 1-hydroxybenzotriazole hydrate (261 mg), cooled to $-23°$ C., and then treated with 1-ethyl-3-(dimethylaminopropyl) carbodiimide Hydrochloride (124 mg). Evaporation after 16 h provided a thick oil which was partitioned bbetween ethylacetate (60 mL) and saturated brine, dried ($MgSO_4$), and evaporated to give a residue which was chromatographed on silica gel (dichloromethane/methanol) to give 161 mg (40%) of the desired product. Mass spectrum: $(M+H)^+ = 626$. Anal. calcd. for $C_{34}H_{51}N_5O_6$: % C, 65.3; H, 8.3; N, 11.2. Found: % C, 65.6; H, 8.3; N, 11.2.

EXAMPLE 158

Boc-Phe-His Amide (at N-2) of 1-Cyclohexyl-2(S),4(R,S)-diamino-3-hydroxy-6-methylheptane.

Treatment of the resultant compound of Example 157 with hydroxylamine followed by reduction of the oxime over platinum oxide gave the desired product.

EXAMPLE 159

Ethoxycarbonyl-Phe-Leu Amide of 1-Cyclohexyl-2(S),3(R,S)-diamino-4-hydroxy-6-methylheptane.

The resultant compound of Example 36 was acetylated using acetic anhydride and the corresponding 3-hydroxy-4-acetoxy compound was isolated by silica gel chromatography. Oxidation to the 3-one using Jones reagent deacetylization using sodium methoxide in methanol, and reductive amination as in Example 158 gave the desired product.

EXAMPLE 160

Ethoxycarbonyl-Phe-His Amide of 2(S)-Amino-1-phenyl-3(R),4(S)-dihydroxy-6-methylheptane.

Using the procedure of Example 13, but replacing Boc-cyclohexylalanine methyl ester with Boc-Phe-OCH$_3$ and then following the procedures of Examples 14 and 29 gave the desired product.

EXAMPLE 161

Cyclic Carbonate of 2(S)-t-Butyloxycarbonylamino-1-cyclohexyl-3(R),4(S)-dihydroxy-6-methylheptane.

The 3(R),4(S)diastereomer of Example 14 was heated with N,N'-carbonyldiimidazole in benzene to give the desired compound in 86% yield.

EXAMPLE 162

D-Ser-Phe-His amide of 2(S)-Amino-1-cyclohexyl-3(R),4(S)-dihydroxy-6-methylheptane.

Following the procedure of Example 15, but replacing the resultant product of Example 14 with the resultant product of Example 161 and replacing Boc-Phe-His with Cbz-D Ser-Phe-His gave the desired N,O-deprotected material. N-deprotection following the procedure of Example 62 followed by O-deprotection with 0.5M NaOH in 50% aq.dioxane, gave the desired compound.

EXAMPLE 163

2(S)-Isobutyrylmercapto-3-phenylpropionyl-Phe-His Amide of 2(S)-Amino-1-cyclohexyl-3(R),4(S)-dihydroxy-6-methylheptane.

S(+)-2-mercapto-3-phenylpropionic acid was prepared as described (Acton, N and Komoriya, A. *Organic Preparation and Procedures Int.* 1982, 14, 381 392.) and acylated with isobutyric anhydride. Replacing TBA-CHA with this acid and using the procedure of Example 21, gave the titled compound.

EXAMPLE 164

2(S)-[(2-Aminoethyl)mercapto]-3-phenypropionyl-Phe-His Amide of 2(S)-Amino-1-cyclohexyl-3(R),4(S)-dihydroxy-6-methylheptane.

(S)-[(2-Aminoethyl)mercapto]-3-phenylpropionic acid was made using literature methodology (Acton, N. and Komoriya, A. *Organic Preparations and Procedures Int.* 1982, 14, 381 392.) Replacing TBA-CHA with this acid and using the procedure of Example 21, gave the titled compound.

EXAMPLE 165

(2S,3R,5R)-2-(t-Butyloxycarbonylamino)-3-hydroxy-7methyl-1-phenyloctane-5-carboxylic Acid Lithium Salt A solution of 27.1 mg (0.075 mmol) of (3R,5R,1'S)-5-[(t-butyloxycarbonylamino)-2-phenylethyl]-3-isobutyl-dihydrofuran-2-(3H)-one (D. J. Kempf, *J. Org. Chem.* 1986, 51, 3921) in 1 mL of dioxane was treated with 185 ul (0.092 mmol) of LiOH (0.5M in H$_2$O) and stirred at ambient temperature for 8 h. Removal of the solvent in vacuo gave the desired compound as a white solid.

EXAMPLE 166

(2S,3R,5R)-3-(t-Butyldimethylsilyloxy)-2-(t-butyloxycarbonylamino)-7-methyl-1-phenyloctane-5-carboxylic Acid t-Butyldimethylsilyl Ester A solution of the resultant compound of Example 165 (0.075 mmol), 42 mg (0.28 mmol) of t-butyldimethylsilyl chloride and 31 mg (0.45 mmol) of imidazole in 0.8 mL of dimethylformamide was allowed to stand at ambient temperature for 2 days. Removal of the solvent in vacuo gave the crude desired compound.

EXAMPLE 167

(2S,3R,5R)-3-(t-(Butyldimethylsilyloxy)-2-(t-butylxycarbonylamino)7-methyl-1-phenyloctane-5-carboxylic Acid Lithium Salt A solution of the crude resultant compound of Example 166 (0.075 mmol) in 2 mL of dioxane was treated with 0.6 mL (0.3 mmol) of LiOH (0.5M in H$_2$O) and allowed to stir at ambient temperature for 2 days. After removal of the solvent, purification by flash column chromatography using 3% methanol/chloroform gave 18.3 mg (49%) of the desired compound (R$_f$ 0.10, 2% methanol/chloroform).

EXAMPLE 168

(2S,3R,5R,8S,9R,10S)-7-Aza-3-(t-butyldimethylsilyloxy)-2-(t-butyloxycarbonylamino)-8-(cyclohexylmethyl)-9,10-dihydroxy-5-isobutyl-12-methyl-1-phenyltridecane Using the coupling procedure of Example 15 but replacing Boc-Phe-His-OH with the resultant compound of Example 167 gave the desired compound in 62% yield after purification by MPLC using 6:1 hexane/ethyl acetate (R$_f$ 0.50, 2:1 hexane/ethyl acetate).

EXAMPLE 169

(2S,3R,5R,8S,9R,10S)-7-Aza-2-(t-butyloxycarbonylamino)-8-(cyclohexylmethyl)-5-isobutyl-12-methyl-1-phenyl-3,9,10-trihydroxytridecane A solution of 16.5 mg (0.023 mmol) of the resultant compound of Example 168 in 1 mL of tetrahydrofuran was treated with 70 mL (0.07 mmol) of tetra-n-butylammmonium fluoride (1M in tetrahydrofuran) and allowed to stir at ambient temperature for 16 h. After concentration in vacuo, separation by MPLC using 2:1 hexane/ethyl acetate gave 10.5 mg (76%) of the desired compound as a white crystalline solid. Mass spectrum: (M+H)+ =605.

EXAMPLE 170

Cbz-6-aminohexanoyl-(4-Methoxy)phenylalanine Benzyl Ester

Using the procedure of Example 72 but replacing 3-benzyloxycarbonylamino 3-methylbutanoic acid with 6-(Cbz-amino)-n-caproic acid and replacing phenylalanine methyl ester with (4-methoxy)phenylalanine benzyl ester gave, after purification by flash column chromatography using 9:1 chloroform/ethyl acetate, a 38% yield of the desired compound.

EXAMPLE 171

Cbz-6-aminohexanoyl-(4-methoxy)phenylalanine

A solution of 2.66 g (5 mmol) of the resultant compound of Example 170 in 60 mL of tetrahydrofuran was cooled to 0° C., treated with 0.63 g (15 mmol) of LiOH in 30 mL of $H_2O$ and allowed to stir for 2 h. After concentration of the solvent, the mixture was partitioned between $H_2O$ and ether, acidified, extracted with ethyl acetate, dried over $MgSO_4$ and concentrated to give 1.55 g (70%) of the desired compound.

EXAMPLE 172

Cbz-6-aminohexanoyl-(4-methoxy)Phe-His Amide of (2S,3R,4S)-2-Amino-1-cyclohexyl-3,4-dihydroxy-6-methylheptane.

Using the procedure of Example 21 but replacing TBA-CHA with the resultant compound of Example 171 gave, after recrystallization from ethyl acetate, a 79% yield of the desired compound. Mass spectrum: $(M+H)^+ = 805$.

EXAMPLE 173

6-Aminohexanoyl-(4-methoxy)Phe-His Amide of (2S,3R,4S)-2-Amino-1-cyclohexyl-3,4-dihydroxy-6-methylheptane Diacetate Salt.

A mixture of 0.97 g (1.2 mmol) of the resultant compound of Example 172 and 0.20 g of 20% palladium on carbon in 150 mL of 95% aqueous acetic acid was shaken in a Parr Apparatus under four atmospheres of $H_2$. After filtration to remove catalyst, the solution was concentrated in vacuo, diluted with 75 mL of $H_2O$, and concentrated by lyophilization to give 0.86 g (91%) of the desired compound as a white solid. Mass spectrum: $(M+H)^+ = 671$.

EXAMPLE 174

[(4-Morpholinyl)carbonyl-D-Phe-His Amide of 2(S)-Amino-1-cyclohexyl-3(R),4(S)-dihydroxy-6-methylheptane.

Using the procedures of Examples 116, 117 and 118 but replacing L-Phe-OCH$_3$ HCl with D-Phe-OCH$_3$ HCl, gave the title compound. Mass spectrum: $(M+H)^+ = 641$.

EXAMPLE 175

Ethyl Hydrogen (α,α-dimethylbenzyl)malonate.

Diethyl (α,α-dimethylbenzyl)malonate was prepared by the congugate addition of phenyl magnesium bromide to diethyl isopropylidenemalonate as described by C. Holmberg [*Liebigs Ann. Chem.*, 748 (1981)]. A solution of this diester (42.1 g, 0.15 mole) in ethanol (100 mL) was treated by dropwise addition with a solution of potassium hydroxide (8.48 g, 0.13 mole) in 100 mL of ethanol. After heating at 90° C. for 1 h and at 50° C. for 20 h, the reaction mixture was evaporated on the rotary evaporator to a residue. The residue was diluted with water and extracted with ether to remove unreacted starting material. The aqueous phase was cooled to 5° C., acidified to pH 3, with 6N HCl and extracted with methylene chloride. The organic layer was washed with brine solution and dried over magnesium sulfate. Evaporation of the solvent gave 27.3 g (84%) of liquid product. NMR (CDCl$_3$): 1.05 (3H, t), 1.6 (6H, s), 3.78 (1H, s), 3.96 (2H, m), 7.2–7.4 (5H, m).

EXAMPLE 176

Ethyl 2(R,S)-[[(4-morpholinyl)carbonyl]amino]-3,3-dimethyl-3-phenylpropionate.

To a solution of ethyl hydrogen (α,α-dimethylbenzyl) malonate (4 g, 0.016 mole) in toluene was added triethylamine (2.23 mL, 0.016 mole) and diphenylphosphoryl azide (4.4 g, 0.016 mole). The reaction mixture was heated at 100° C. for 2.5 h, cooled to 5° C., and treated with 1.4 mL (0.016 mole) of morpholine. After stirring overnight at room temperature, the toluene solution was washed successively with 1N HCl and aqueous sodium bicarbonate solution. The dried organic solution was evaporated to a residue which was purified by column chromatography on silica gel. There was obtained 3.7 g (69%) of product after trituration with hexane, mp 93°–94° C.

Anal. calcd. for $C_{18}H_{26}N_2O_4$: C, 64.65; H, 7.84; N, 8.38. Found: C, 64.72; H, 7.95; N, 8.33.

EXAMPLE 177

2(R,S)-[[(4-Morpholinyl)carbonyl]amino]-3,3-dimethyl-3-phenylpropionic Acid.

A solution of the product form Example 176 (2 g, 5.99 mmole) in dioxane (10 mL) was treated with 0.26 g (6.5 mmol) of sodium hydroxide in 5 mL of water. After stirring for 16 h at 35° C., the reaction was worked up as described in Example 175 to give a 93% yield of product.

EXAMPLE 178

2(R,S)-[[(4-Morpholinyl)carbonyl]amino]-3,3-dimethyl-3-phenylpropionyl-His Amide of 2(S)-Amino-1-cyclohexyl-3(R),4(S)-dihydroxy-6-methylheptane.

The product from Example 20 was deprotected with HCl/methanol and coupled to the product from Example 177 the procedure described in Example 5 but modified as follows. HOBT was not used in the coupling and the reaction time was 20 h. There was obtained an 80% yield of the desired product. Mass spectrum: $(M+H)^+ = 669$.

EXAMPLE 179

H-Isonipecotyl-(4-OCH$_3$)Phe-His Amide of 2(S)-Amino-1-cyclohexyl-3(R),4(S)-dihydroxy-6-methylheptane Diacetic Acid Salt.

Using the procedure of Examples 67 and 68, but replacing Cbz-isonipecotyl-Phe with Cbz-isonipecotyl-(4-OCH$_3$)-Phe gave the desired product. Mass spectrum: $(M+H)^+ = 669$ (free base).

EXAMPLE 180

H-[(β,β-di-Me)-beta-Ala]-(4-OCH$_3$)Phe-His Amide of 2(S)-Amino-1-cyclohexyl-3(R),4(S)-dihydroxy-6-methylheptane Diacetic Acid Salt.

Using the procedures of Examples 74 and 75, but replacing Cbz-[(β,β-di-Me)-β-Ala]-Phe with Cbz-[(β,β-di-Me)-β-Ala]-(OCH$_3$)Phe gave the desired product. $(M+H)^+ = 657$ (free base).

EXAMPLE 181

2(S)-t-Butyloxycarbonylamino-1-cyclohexyl-3(R)-hydroxy-6-methylheptan-4-one

To a stirred −63° C. solution of oxalyl chloride (784 mg, 6.18 mmol) in dry dichloromethane (15 mL) was added dry dimethylsulfoxide (708 mg, 9.06 mmol) dropwise over 5 minutes. After another 5 minutes, Boc-cyclohexylalaninol (1.06 g, 4.12 mmol) in dichloromethane (5 mL) was added dropwise over 5 minutes, and 5 minutes later, triethylamine (1.67 g, 16.48 mmol) was added similarly, $ZnI_2$ (300 mg, 0.94 mmol) was added over 5 minutes. After stirring for 2 minutes, trimethylsilyl cyanide (1.43g, 14.42 mmol) was added and the mixture was warmed to room temperature for 1 hour. The mixture was then cooled to 0° C. and isobutylmagnesium chloride (22.0 mL of a 2M soln. in ether) was added. After warming to room temperature for 4 hours, the mixture was poured into 1M $H_3PO_4$ (40 mL)/ice (50 mL) and extracted with ethyl acetate. The combined organic phase was washed sequentially with 1M $H_3PO_4$, water, satd. $NaHCO_3$, and brine. Drying ($MgSO_4$), filtering, and evaporating provided 1.75 g of an oil which was dissolved in THF (75 mL) and treated with 1M $H_3PO_4$ (25 mL) for 18 hours at 5° C. The solution was partitioned between ethyl acetate/brine, and the resulting organic phase was washed sequentially with brine, satd. $NaHCO_3$, and brine. Drying ($MgSO_4$), filtering, and evaporating provided the desired product (1.39 g, 99%) which was used directly in the next step.

EXAMPLE 182

2(S)-t-Butyloxycarbonylamino-1-cyclohexyl-3(R),4(S)-dihydroxy-6-methylheptane To a stirred solution of 2(S)-t-Butyloxycarbonylamino-1-cyclohexyl-3(R)-hydroxy-6-methylheptan4-one (200 mg, 0.586 mmol) in THF (10 mL) was added $NaBH_4$ (22 mg, 0.586 mmol). After 2 hours, the solvent was evaporated and the residue was partitioned between ethyl acetate and brine. The organic phase was washed (brine), dried ($MgSO_4$), filtered and evaporated. The residue was recrystallized from methylcyclohexane to give 76 mg (38%) of the desired product. M.p. 130°-131° C. The mother liquor was chromatographed (silica gel, ether/hexane) to afford 43 mg (21%) more.

EXAMPLE 183

(2S,3R,5R,8S,9R,10S)-7-Aza-2-(t-Butyloxycarbonylamino)-8-(cyclohexylmethyl)-12-methyl-5-(4-pentenyl)-1-phenyl-3,9,10-trihydroxytridecane Using the procedures of Examples 165-169, but replacing (3R,5R,1′S)-5-[(t-butyloxycarbonylamino)-2-phenylethyl]-3-isobutyldihydrofuran-2-(3H)-one with (3R,5R,1′S)-5-[(t-butyloxycarbonylamino)-2-phenylethyl]-3-(4-pentenyl)dihydrofuran-2-(3H)-one (D. J. Kempf, *J. Org. Chem.* 1986, 51, 3921) gave the desired compound in 52% yield after purification by MPLC using 2:1 hexane/ethyl acetate. Mass spectrum: $(M+H)^+ = 617$.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptonate, hexanoate, fumarate, hydrochloride, hydrobromide, hydroiodide, 2 hydroxy-ethanesulfonate, lactate, maleate, methanesulfonate, nicotinate, 2 naphthalenesulfonate, oxalate, pamoate, pectinate, persulfate, 3 phenylpropionate, picrate, pivalate, propionate, succinate, tartrate, thiocyanate, tosylate, and undecanoate. Also, the basic nitrogen containing groups can be quaternized with such agents as loweralkyl halides, such as methyl, ethyl, propyl, and butyl chloride, bromides, and iodides; dialkyl sulfates like dimethyl, diethyl, dibutyl., and diamyl sulfates, long chain halides such as decyl, lauryl, myristyl and stearyl chlorides, bromides and iodides, aralkyl halides like benzyl and phenethyl bromides, and others. Water or oil soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases.

The compounds of the present invention can also be used in the form of esters. Examples of such esters include a hydroxyl substituted compound of formula I which has been acylated with a blocked or unblocked amino acid residue, a phosphate function, or a hemisuccinate residue. The amino acid esters of particular interest are glycine and lysine; however, other amino acid residues can also be used. These esters serve as prodrugs of the compounds of the of these substances in the gastrointestinal tract. The preparation of the pro drug esters is carried out reacting a hydroxyl-substituted compound of formula I with an activated amino acyl, phosphoryl or hemisuccinyl, derivative. The resulting product is then deprotected to provide the desired pro-drug ester.

The novel compounds of the present invention possess an excellent degree of activity and specificity in treating renin-associated hypertension in a host. The ability of the compounds of the invention to inhibit human renal renin can be demonstrated in vitro by reacting a selected compound at varied concentrations with human renal renin, free from acid proteolytic activity, and with renin substrate (human angiotensinogen) at 37° C. and pH 6.0. At the end of the incubation, the amount of angiotensin I formed is measured by radioimmunoassay and the molar concentration required to cause 50% inhibition, expressed as the $IC_{50}$, is calculated. When tested in accordance with the foregoing procedure, the compounds of the invention demonstrated $IC_{50}$'s in the range of $10^{-5}$ to $10^{-10}$ M as seen in Table I.

TABLE I

| Example Number | $IC_{50}$ (nM) | Example Number | $IC_{50}$ (nM) |
|---|---|---|---|
| 3 | 4000 | 63 | 0.45 |
| 6 | 50 | 64 | 3 |
| 15 | 1.5 | 67 | 0.8 |
| 16 | 70 | 68 | 1 |
| 17 | 35 | 69 | 0.81 |
| 18 | 95 | 70 | 2.5 |
| 21 | 2 | 74 | 0.7 |
| 22 | 1.5 | 75 | 0.4 |
| 23 | 10 | 76 | 0.5 |
| 24 | 2 | 77 | 0.98 |
| 25 | 20 | 81 | 0.6 |

TABLE I-continued

| Example Number | IC$_{50}$ (nM) | Example Number | IC$_{50}$ (nM) |
|---|---|---|---|
| 26 | 1.5 | 82 | 0.6 |
| 27 | 7 | 83 | 0.6 |
| 28 | 80 | 84 | 10 |
| 29 | 0.6 | 85 | 0.4 |
| 30 | 0.75 | 87 | 0.55 |
| 31 | 1 | 88 | 0.6 |
| 32 | 2 | 89 | 1 |
| 33 | 5 | 90 | 0.4 |
| 34 | 1.5 | 91 | 0.3 |
| 35 | 1 | 92 | 0.5 |
| 36 | 0.4 | 93 | 0.55 |
| 37 | 0.5 | 97 | 0.3 |
| 39 | 2 | 101 | 5 |
| 43 | 5 | 102 | 0.6 |
| 46 | 1.5 | 103 | 1 |
| 47 | 1 | 108 | 0.55 |
| 49 | 2 | 111 | 0.5 |
| 54 | 0.95 | 114 | 1.3 |
| 55 | 2 | 115 | 1 |
| 56 | 5.5 | 118 | 0.5 |
| 57 | 7.5 | 124 | 0.65 |
| 58 | 7 | 127 | 0.75 |
| 61 | 0.55 | 141 | 5.5 |
| 62 | 2 | 143 | 0.3 |
| 169 | 6.0 | 178 | 2 |
| 173 | 0.9 | 179 | 1 |
| 174 | 12 | 180 | 0.8 |
| 183 | 12 | | |

The compounds of the invention may also be used with one or more antihypertensive agents selected from the group consisting of diuretics, and/or β-adrenergic blocking agents, central nervous system acting agents, adrenergic neuron blocking agents, vasodilators, angiotensin I converting enzyme inhibitors, and other antihypertensive agents.

Total daily dose administered to a host in single or divided doses may be in amounts, for example, from 0.001 to 10 mg/kg body weight daily and more usually 0.01 to 1 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, by inhalation spray, rectally, or topically in dosage unit formulations containing conventional nontoxic pharmaceutically acceptable carriers, adjuvants, and vehicles as desired. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A process for the preparation of a compound of the formula:

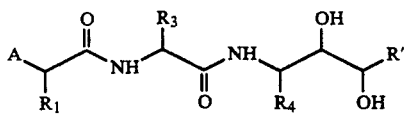

wherein A is hydrogen, loweralkyl, arylalkyl, —OR$_{10}$ or —SR$_{10}$ wherein R$_{10}$ is hydrogen, loweralkyl or aminoalkyl; or A is —NR$_{11}$R$_{12}$ wherein R$_{11}$ and R$_{12}$ are independently selected from hydrogen, loweralkyl, aminoalkyl, cyanoalkyl and hydroxyalkyl; or A is

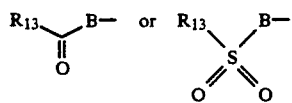

wherein B is NH, alkylamino, S, O, CH$_2$ or CHOH and R$_{13}$ is loweralkyl, cycloalkyl, aryl, arylalkyl, alkoxy, alkenyloxy, hydroxyalkoxy, dihydroxyalkoxy, arylalkoxy, arylalkoxyalkyl, amino, alkylamino, dialkylamino, (hydroxyalkyl)(alkyl)amino, aminoalkyl, alkylaminoalkyl, (N-protected)aminoalkyl, (N-protected)(alkyl)aminoalkyl, dialkylaminoalkyl, (heterocyclic)alkyl or an unsubstituted or a monosubstituted heterocyclic wherein the substituent is hydroxy, oxo, amino, alkylamino, dialkylamino or loweralkyl, provided that when the heterocyclic is unsaturated the substituent is not oxo;

R₁ is loweralkyl, cycloalkylmethyl, benzyl, 4-methoxybenzyl, halobenzyl, (1-naphthyl)methyl, (2-naphthyl)methyl, (4-imidazolyl)methyl, (alpha,alpha)-dimethylbenzyl, 1-benzyloxyethyl, phenethyl, phenoxy, thiophenoxy or anilino; provided that when R₁ is phenoxy, thiophenoxy or anilino, then B is CH₂ or CHOH or A is hydrogen;

R₂ is hydrogen or loweralkyl;

R₃ is loweralkyl, loweralkenyl, ((alkoxy)alkoxy)alkyl, (thioalkoxy)alkyl, benzyl or heterocyclic ring substituted methyl;

R₄ is loweralkyl, cycloalkylmethyl or benzyl; and

R' is hydrogen, loweralkyl, vinyl or arylalkyl; comprising the steps of (a) coupling an N-protected amino acid of the formula

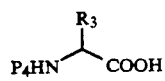

wherein R₃ is defined as above and P₄ is an N-protecting group with a compound of the formula:

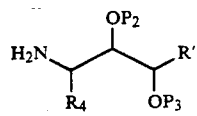

wherein R' and R₄ are defined as above and P₂ and P₃ are independently selected from hydrogen and an O-protecting group, followed by (b) removing the N-protecting group P₄ from the resulting product of step (a) and then coupling the N-deprotected product of step (a) with a compound of the formula:

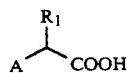

wherein A and R₁ are defined as above.

2. A process for the preparation of a compound of the formula:

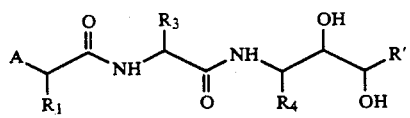

wherein A is hydrogen, loweralkyl, arylalkyl, —OR₁₀ or —SR₁₀ where R₁₀ is hydrogen, loweralkyl or aminoalkyl; or A is —NR₁₁R₁₂ wherein R₁₁ is R₁₂ are independently selected from hydrogen, loweralkyl, aminoalkyl, cyanoalkyl and hydroxyalkyl; or A is

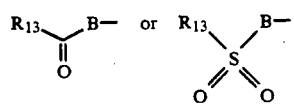

wherein B is NH, alkylamino, S, O, CH₂ or CHOH and R₁₃ is loweralkyl, cycloalkyl, aryl, arylalkyl, alkoxy, alkenyloxy, hydroxyalkoxy, dihydroxyalkoxy, arylalkoxy, arylalkoxyalkyl, amino, alkylamino, dialkylamino, (hydroxyalkyl)(alkyl)amino, aminoalkyl, alkylaminoalkyl, (N-protected)aminoalkyl, (N-protected)(alkyl)aminoalkyl, dialkylaminoalkyl, (heterocyclic)alkyl or an unsubstituted or a monosubstituted heterocyclic wherein the substituent is hydroxy, oxo, amino, alkylamino, dialkylamino or loweralkyl, provided that when the heterocyclic is unsaturated the substituent is not oxo;

R₁ is loweralkyl, cycloalkylmethyl, benzyl, 4-methoxybenzyl, halobenzyl, (1-naphthyl)methyl, (2-naphthyl)methyl, (4-imidazolyl)methyl, (alpha,alpha)-dimethylbenzyl, 1-benzyloxyethyl, phenethyl, phenoxy, thiophenoxy or anilino; provided that when R₁ is phenoxy, thiophenoxy or anilino, then B is CH₂ or CHOH or A is hydrogen;

R₂ is hydrogen or loweralkyl;

R₃ is loweralkyl, loweralkenyl, ((alkoxy)alkoxy)alkyl, (thioalkoxy)alkyl, benzyl or heterocyclic ring substituted methyl R₄ is loweralkyl, cycloalkylmethyl or benzyl; and R' is hydrogen, loweralkyl, vinyl or arylalkyl; comprising coupling a compound of the formula:

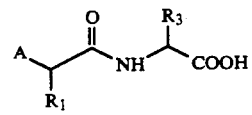

wherein A, R₁ and R₃ are defined as above with a compound of the formula:

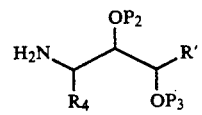

wherein R' and R₄ are defined as above and P₂ and P₃ are independently selected from hydrogen and an O-protecting group.

3. A process for the preparation of a compound of the formula:

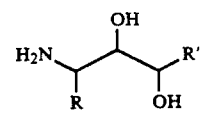

wherein R is loweralkyl, cycloalkylmethyl or benzyl and R' is hydrogen, loweralkyl or arylalkyl comprising (a) reacting an aldehyde of the formula (1)

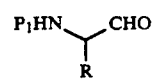 (1)

wherein R is defined as above and P₁ is an N-protecting group with an ylide to provide a compound of the formula (2)

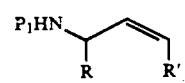 (2)

wherein R, R' and P₁ are defined as above:

(b) oxidizing the compound of formula (2) to provide diol (3)

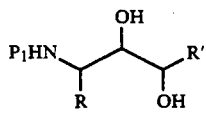 (3)

wherein R, R' and P₁ are defined as above; and
(c) removing the N-protecting group.

4. The process of claim 3 wherein the ylide is a phosphonium ylide.

5. The process of claim 3 wherein the oxidizing agent is OsO₄.

6. The process of claim 3 wherein R is cyclohexylmethyl, P₁ is t-butyloxycarbonyl, the ylide is isopentyltriphenylphosphonium bromide and the oxidizing agent is OsO₄.

7. A process for the preparation of a compound of the formula:

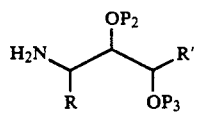

wherein P₂ and P₃ are independently selected from hydrogen and an O-protecting group;
R is loweralkyl, cycloalkylmethyl or benzyl; and
R' is loweralkyl, vinyl or arylalkyl comprising
(a) converting an aldehyde of the formula (1)

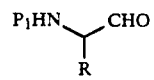 (1)

wherein
R is defined as above and P₁ is an N-protecting group to the cyanohydrin (4)

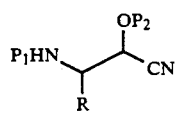 (4)

wherein
R and P₁ are defined as above and P₂ is hydrogen or an O-protecting group;
(b) reacting the cyanohydrin (4) with an organometallic reagent to provide the ketone (5)

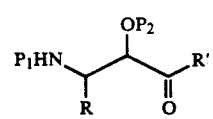 (5)

wherein R, R', P₁ and P₂ are defined as above;
(c) reducing the ketone to an alcohol; and
(d) removing the N-protecting group.

8. The process of claim 7 wherein the organometallic reagent is a Grignard reagent.

9. A process for the preparation of a compound of the formula:

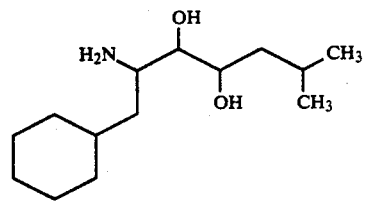

comprising
(a) reacting

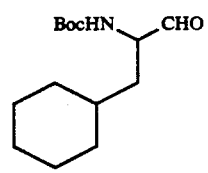

with isopentyltriphenylphosphonium bromide to provide 2(S)-t-butyloxycarbonylamino-1-cyclohexyl-6-methylhept-3-ene;
(b) oxidizing the product of step (a) with OsO₄ to provide 2(S)-t-butyloxycarbonylamino-1-cyclohexyl-3,4-dihydroxy-6-methylheptane; and
(c) removing the N-protecting group.

10. A process for the preparation of a compound of the formula:

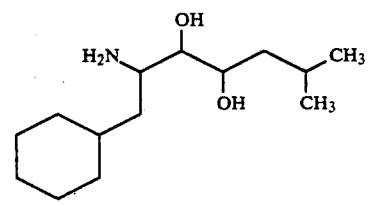

comprising
(a) reacting

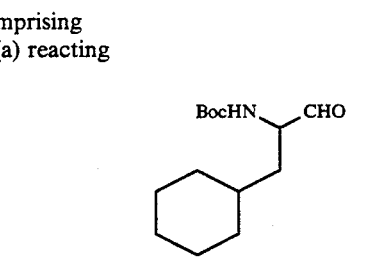

with trimethylsilylcyanide to form

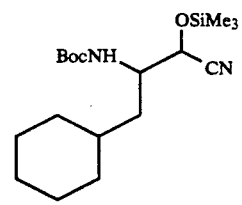

(b) reacting the product of step (a) with isobutylmagnesium chloride, followed by treatment under acidic conditions to provide 2(S)-t-butyloxycarbonylamino-1-cyclohexyl-3-hydroxy-6-methylheptan-4-one;
(c) reducing the product of step (b) with NaBH₄; and
(d) removing the N-protecting group.

11. A process for the preparation of a compound of the formula:

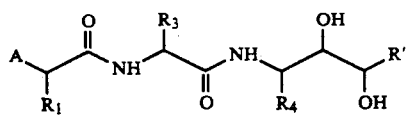

wherein A is hydrogen, loweralkyl, arylalkyl, —OR$_{10}$ or —SR$_{10}$ wherein R$_{10}$ is hydrogen, loweralkyl or aminoalkyl; or A is —NR$_{11}$R$_{12}$ wherein R$_{11}$ and R$_{12}$ are independently selected from hydrogen, loweralkyl, aminoalkyl, cyanoalkyl and hydroxyalkyl; or A is

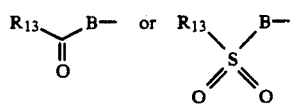

wherein B is NH, alkylamino, S, O, CH$_2$ or CHOH and R$_{13}$ is loweralkyl, cycloalkyl, aryl, arylalkyl, alkoxy, hydroxyalkoxy, dihydroxyalkoxy, arylalkoxy, arylalkoxyalkyl, amino, alkylamino, dialkylamino, (hydroxyalkyl)(alkyl)amino, aminoalkyl, alkylaminoalkyl, (N-protected)aminoalkyl, (N-protected)(alkyl)aminoalkyl, dialkylaminoalkyl, (heterocyclic)alkyl or an unsubstituted or a monosubstituted heterocyclic wherein the substituent is hydroxy, oxo, amino, alkylamino, dialkylamino or loweralkyl, provided that when the heterocyclic is unsaturated the substituent is not oxo;

R$_1$ is loweralkyl, cycloalkylmethyl, benzyl, 4-methoxybenzyl, halobenzyl, (1-naphthyl)methyl, (2-naphthyl)methyl, (4-imidazolyl)methyl, (alpha,alpha)-dimethylbenzyl, 1-benzyloxyethyl, phenethyl, phenoxy, thiophenoxy or anilino; provided that when R$_1$ is phenoxy, thiophenoxy or anilino, then B is CH$_2$ or CHOH or A is hydrogen;

R$_2$ is hydrogen or loweralkyl;

R$_3$ is loweralkyl, ((alkoxy)alkoxy)alkyl, (thioalkoxy)alkyl, benzyl or heterocyclic ring substituted methyl;

R$_4$ is loweralkyl, cycloalkylmethyl or benzyl; and

R' is hydrogen, loweralkyl or aralkyl; comprising oxidizing a compound of the formula:

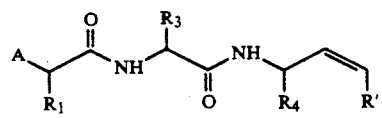

wherein A, R$_1$, R$_3$, R$_4$ and R' are defined as above.

* * * * *